United States Patent
Yan et al.

(10) Patent No.: US 12,156,879 B2
(45) Date of Patent: Dec. 3, 2024

(54) COMBINING BACE1 INHIBITORS WITH mGluR AGONISTS FOR ALZHEIMER'S DISEASE THERAPY

(71) Applicant: University of Connecticut, Farmington, CT (US)

(72) Inventors: Riqiang Yan, Farmington, CT (US); Brati Das, Farmington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 554 days.

(21) Appl. No.: 17/108,227

(22) Filed: Dec. 1, 2020

(65) Prior Publication Data
US 2021/0161910 A1    Jun. 3, 2021

Related U.S. Application Data

(60) Provisional application No. 62/942,558, filed on Dec. 2, 2019.

(51) Int. Cl.
| | | |
|---|---|---|
| *A61K 31/549* | (2006.01) | |
| *A61K 31/4439* | (2006.01) | |
| *A61K 31/506* | (2006.01) | |
| *A61K 31/541* | (2006.01) | |
| *A61P 25/28* | (2006.01) | |

(52) U.S. Cl.
CPC ........ *A61K 31/549* (2013.01); *A61K 31/4439* (2013.01); *A61K 31/506* (2013.01); *A61K 31/541* (2013.01); *A61P 25/28* (2018.01)

(58) Field of Classification Search
CPC .............. A61K 31/549; A61K 31/4439; A61K 31/506; A61K 31/541; A61P 25/28
See application file for complete search history.

(56) References Cited

U.S. PATENT DOCUMENTS

2018/0271832 A1*   9/2018   Schon ................ A61K 31/192

FOREIGN PATENT DOCUMENTS

WO    WO-2004056814 A1 *   7/2004   ........... C07D 413/12

OTHER PUBLICATIONS

Neumann, U., R. Machauer and D. Shimshek, "The β-secretase (BACE) inhibitor NB-360 in preclinical models: From amyloid-β reduction to downstream disease-relevant effects", Br J Pharmacol. 2019; 179: pp. 3435-3446. (Year: 2019).*
Niswender, C. and P. Conn, "Metabotropic Glutamate Receptors: Physiology, Pharmacology, and Disease", Annu. Rev. Pharmacol. Toxicol., 2010, 50: 295-322. (Year: 2010).*
Evin, "Future Therapeutics in Alzheimer's Disease: Development Status of BACE Inhibitors" BioDrugs (2016), 30: pp. 173-194. (Year: 2016).*
Srivastava, A., B. Das, A. Yao and R. Yan, "Metabotropic Glutamate Receptors in Alzheimer's Disease Synaptic Dysfunction: Therapeutic Opportunities and Hope for the Future", Journal of Alzheimer's Disease (2020), 78(4), pp. 1345-1361. (Year: 2020).*
Egan et al., "Randomized Trial of Verubecestat for Mild-to-Moderate Alzheimer's Disease" N. Engl. J. Med. 378:1691-1703 (May 3, 2018).
Mullard, "BACE failures lower AD expectations, again" Nature Reviews Drug Discovery 17:385 (May 30, 2018).
NCT01739348; An Efficacy and Safety Trial of Verubecestat (MK-8931) in Mild to Moderate Alzheimer's Disease (P07738) (EPOCH)—Clinical Trials.gov last update posted Oct. 24, 2018, pp. 1-14.
Janssen drops the BACE as Alzheimer's candidate joins fail list—May 18, 2018 https://www.fiercebiotech.com/biotech/janssen-drops-bace-as-alzheimer-s-candidate-joins-fail-list (accessed Jul. 2, 2023, pp. 1-2).
Eisai and Biogen to Discontinue Phase III Clinical Studies of BACE Inhibitor Elenbecestat in Early Alzheimer's Disease—Sep. 13, 2019; https://investors.biogen.com/news-releases/news-release-details/eisai-and-biogen-discontinue-phase-iii-clinical-studies-bace (accessed Jul. 2, 2023, pp. 1-2).

* cited by examiner

*Primary Examiner* — Amanda L. Aguirre
*Assistant Examiner* — Sagar Patel
(74) *Attorney, Agent, or Firm* — McDonnell Boehnen Hulbert & Berghoff LLP

(57) ABSTRACT

Disclosed pharmaceutical compositions including a Beta site APP Cleaving Enzyme (BACE1) inhibitor and an metabotropic glutamate receptor (mGluR) agonist, and methods for use of such compositions to treat Alzheimer's disease (AD), Down's syndrome, Parkinson's disease, vascular dementia, Dementia with Lewy Bodies, dementia, and/or frontal temporal dementia.

15 Claims, 22 Drawing Sheets

BACE1$^{+/+}$  BACE1$^{+/+}$ + Lanabecestat  BACE1$^{+/+}$ + Verubebecestat

COMBINING BACE1 INHIBITORS WITH mGluR AGONISTS FOR ALZHEIMER'S DISEASE THERAPY

CROSS REFERENCE

This application claims priority to U.S. Provisional Application Ser. No. 62/942,558 filed Dec. 2, 2019, incorporated by reference herein in its entirety.

FEDERAL FUNDING STATEMENT

This invention was made with government support under grants RF1AG058261, AG025493, NS074256, and AG046929 from the National Institutes of Health. The government has certain rights in the invention.

BACKGROUND

Typical clinical symptoms of Alzheimer's disease (AD) are gradual loss of memory and cognitive ability. The abnormal elevation of β-amyloid peptides (Aβ) in AD patients' brains is recognized as one of the earliest changes, and toxic Aβ can induce a cascade of pathological events that include the formation of amyloid plaques, neurofibrillary tangles, and neurodegeneration. Aβ is generated from amyloid precursor protein (APP) through sequential cleavages by β- and γ-secretase. BACE1, β-site amyloid precursor protein cleaving enzyme 1, was discovered to be the sole β-secretase that initiates the production of β-amyloid peptide (Aβ), and BACE1 inhibition or deletion reduces amyloid deposition in brains of AD patients and animal models. However, cognitive function is not improved using BACE1 inhibitors based on clinical ratings of dementia among prodromal AD patients, with measures actually worsening in some patients, resulting in the early termination of clinical trials.

SUMMARY

In one aspect, the disclosure provides methods for treating Alzheimer's disease (AD), Down's syndrome, Parkinson's disease, vascular dementia, Dementia with Lewy Bodies, and/or frontal temporal dementia, comprising administering to a subject having AD, Down's syndrome, Parkinson's disease, vascular dementia, Dementia with Lewy Bodies, and/or frontal temporal dementia, an amount effective to treat AD of:
(a) a Beta site APP Cleaving Enzyme (BACE1) inhibitor; and
(b) an metabotropic glutamate receptor (mGluR) agonist.

In one embodiment, the BACE1 inhibitor is selected from the group consisting of SCH1682496 (6-(3-chloro-5-(5-prop-1-yn-1-yl)pyridin-3-yl)thiophen-2-yl)-2-imino-3,6-dimethyltetrahydropyrimidin-4(1H)-one); LY2811376, verubecestat, lanabecestat, umibecestat, elenbecestat, atabecestat, LY3202626, AZD3839, pharmaceutically acceptable salts thereof, and/or combinations thereof. In another embodiment, the mGlu agonist comprises an mGluR1 agonist, an mGluR5 agonist, and/or an mGluR7 agonist. In a further embodiment, the mGluR agonist is selected from the group consisting of (RS)-2-Chloro-5-hydroxyphenylglycine (CHPG), 3-Chloro-4-[(5-chloro-2-pyridinyl)oxy]phenyl]-2-pyridinecarboxamide (VU 0422288); (S)-3,5-dihydroxyphenylglycine (DHPG); (R,S)-3,5-dihydroxyphenylglycine, quisqualate, trans-azetidine-2,3-dicarboxylic acid, 3-hydroxyphenylglycine; VU6000799, VU6000790, ACPT1, (R,S)-PPG, Ro 67-7476, Ro0711401, pharmaceutically acceptable salts thereof, and/or combinations thereof. In one embodiment, the method comprises administering to the subject one BACE inhibitor and one mGluR1 agonist, mGluR5 agonist, and/or mGluR7 agonist. In other embodiments, the BACE1 inhibitor and the mGluR agonist are co-administered, or they are administered sequentially. In another embodiment, the subject is a human subject. In various embodiments, the human subject possesses an apolipoprotein E (APOE) ε4 allele and/or mutations associated with AD disease incidence and/or progression in one or more of an amyloid precursor protein (APP) gene, a presenilin 1 (PS1) gene, and/or a Trem 2 gene.

In another aspect, the disclosure provides pharmaceutical composition, comprising:
(a) a BACE1 inhibitor; and
(b) an mGluR agonist.

In one embodiment, the BACE1 inhibitor is selected from the group consisting of SCH1682496 (6-(3-chloro-5-(5-prop-1-yn-1-yl)pyridin-3-yl)thiophen-2-yl)-2-imino-3,6-dimethyltetrahydropyrimidin-4(1H)-one); LY2811376, verubecestat, lanabecestat, umibecestat, elenbecestat, atabecestat, LY3202626, AZD3839, pharmaceutically acceptable salts thereof, and/or combinations thereof. In another embodiment, the mGlu agonist comprises an mGluR1 agonist, an mGluR5 agonist, and/or an mGluR7 agonist. In a further embodiment, the mGlu agonist (RS)-2-Chloro-5-hydroxyphenylglycine (CHPG), 3-Chloro-4-[(5-chloro-2-pyridinyl)oxy]phenyl]-2-pyridinecarboxamide (VU 0422288); (S)-3,5-dihydroxyphenylglycine (DHPG); (R,S)-3,5-dihydroxyphenylglycine, quisqualate, trans-azetidine-2,3-dicarboxylic acid, 3-hydroxyphenylglycine; VU6000799, VU6000790, ACPT1, (R,S)-PPG, Ro 67-7476, Ro0711401, pharmaceutically acceptable salts thereof, and/or combinations thereof.

DETAILED DESCRIPTION

Figure 1A:
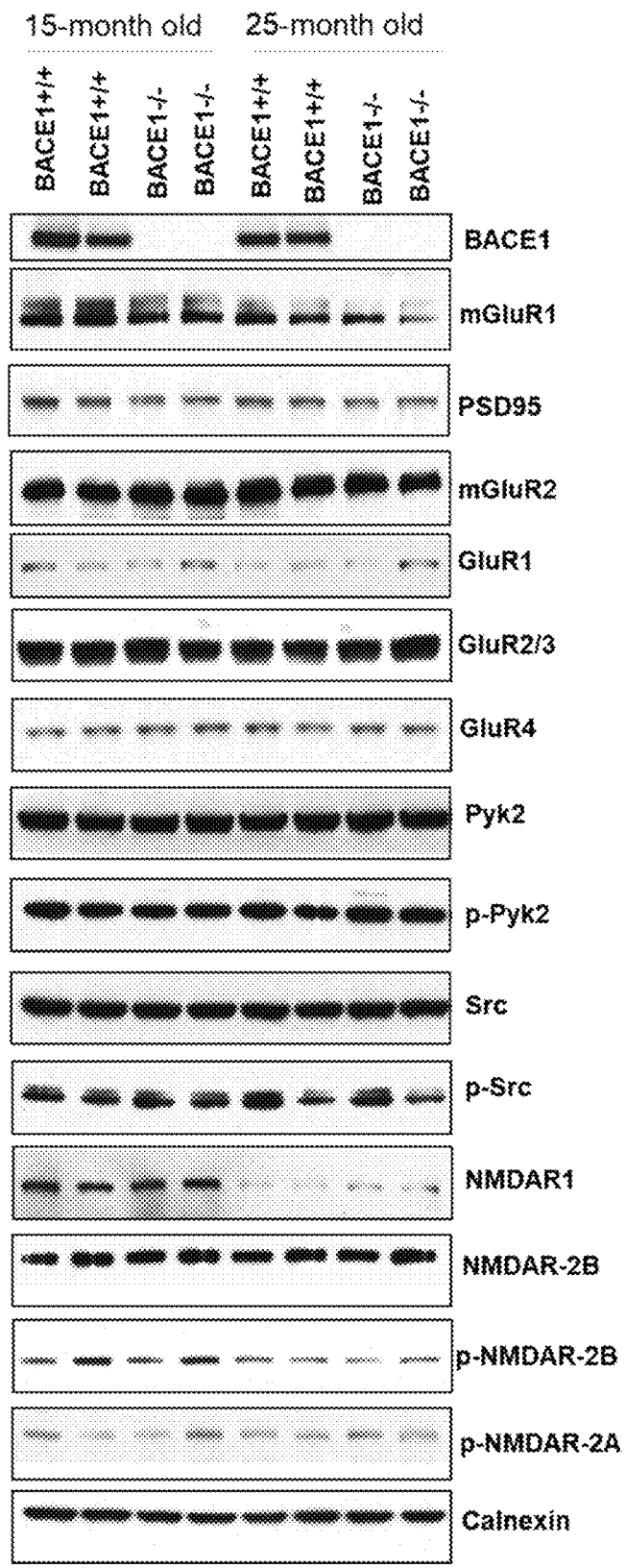
FIG. 1A-1D: BACE1 deficiency causes an age-dependent reductions in synaptic proteins PSD-95 and mGluR1. (A) Hippocampal synaptosomes prepared from 15- and 25-month-old mice were examined for possible changes in synaptic proteins as indicated. While levels of most synaptic proteins were not significantly differed between wild type (WT) and BACE1-null samples, mGluR1 and PSD-95 were clearly reduced in BACE1-null samples. (B) Bar graphs showing a significant change in levels of mGluR1 and PSD-95 in aging mice. (C) Synaptosomal samples prepared from animals with BACE1 inhibitor treatments Lanabecestat (AZD3293) at 0.5 mg/kg or Verubecestat at 3 mg/kg also reduce PSD95,Synaptophysin and mGluR2. (n=3 independent experiments *, P<0.05; Student's t test). Long-term use of BACE1 inhibitors Lanabecestat (AZD3293) and Verubecestat (MK-8931), also decrease significantly the levels of PSD95, mGluR2 and Synaptophysin in synaptosome fraction ((FIG. 1C,D, N=3 experiments, two pairs each, *P<0.05, Student's t-test).

As used herein and unless otherwise indicated, the terms "a" and "an" are taken to mean "one", "at least one" or "one or more". Unless otherwise required by context, singular terms used herein shall include pluralities and plural terms shall include the singular. All embodiments of any aspect of the disclosure can be used in combination, unless the context clearly dictates otherwise.

In a first aspect, the disclosure provides methods for treating Alzheimer's disease (AD), Down's syndrome, Parkinson's disease, vascular dementia, Dementia with Lewy Bodies, and/or frontal temporal dementia, comprising administering to a subject having AD, Down's syndrome, Parkinson's disease, vascular dementia, Dementia with Lewy Bodies, and/or frontal temporal dementia, an amount effective to treat AD of:

(a) a Beta site APP Cleaving Enzyme (BACE1) inhibitor; and
(b) an metabotropic glutamate receptor (mGluR) agonist.

As disclosed herein, the inventors have discovered that a therapy combining BACE1 inhibitors for reducing amyloid deposition and an mGluR positive allosteric modulator for counteracting BACE1-mediated synaptic deficits is a more effective approach for treating subjects with a variety of neurological issues.

As used here, the terms "treat", "treatment", and "treating" mean:

(i) inhibiting the progression the disease or disorder, including but not limited to inhibiting progression of dementia associated with the disease or disorder;
(ii) inhibiting the disease or disorder; for example, inhibiting a disease, condition or disorder in an individual who is experiencing or displaying the pathology or symptomatology of the disease, condition or disorder, including but not limited to inhibiting dementia associated with the disease or disorder; and/or
(iii) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease, including but not limited to decreasing severity of dementia associated with the disease or disorder.

As used herein, the phrase "an amount effective" refers to the amount of active compound or pharmaceutical agent that elicits the biological or medicinal response that is being sought in a tissue, system, animal, individual or human by a researcher, veterinarian, medical doctor or other clinician, such as those noted above.

Amyloid beta peptide (Aβ) is a primary component of β amyloid fibrils and plaques which play a role in Alzheimer's disease (AD) as well as other diseases such as Down's syndrome and Parkinson's disease. Aβ peptides are created from the proteolytic cleavage of amyloid precursor protein (APP) near the N-terminus by β-secretase activity and near the C-terminus by γ-secretase activity. The primary β-secretase producing Aβ peptide is Beta site APP Cleaving Enzyme (BACE1). Any suitable BACE1 inhibitor capable of reducing Aβ levels may be used in the methods of the disclosure. In various non-limiting embodiments, the BACE1 inhibitor is selected from the group including but not limited to SCH1682496 (6-(3-chloro-5-(5-prop-1-yn-1-yl)pyridin-3-yl)thiophen-2-yl)-2-imino-3,6-dimethyltetrahydropyrimidin-4(1H)-one) (available, for example, from Medkoo Biosciences, Inc., Morrisville, NC);

LY2811376 (available, for example, from Selleckchem (Houston, TX)

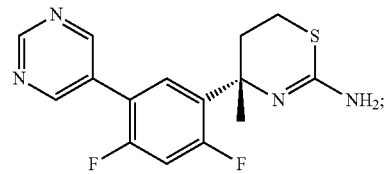 [SMILES: C[C@@]1(c2cc(-c3cncnc3)c(F)cc2F)CCSC(N)=N1]

Verubecestat (MK-8931) (available, for example, from Medkoo Biosciences, Inc., Morrisville, NC)

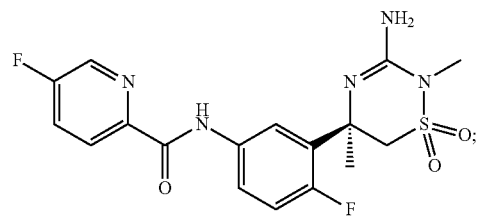 [SMILES: CN1C(N)=N[C@](C)(c2cc(NC(=O)c3ccc(F)cn3)ccc2F)CS1(=O)=O]

Lanabecestat (AZD3293) (available, for example, from Medkoo Biosciences, Inc., Morrisville, NC)

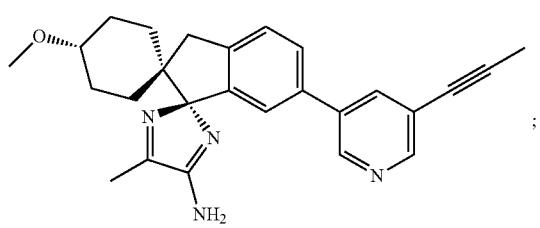 [SMILES: CC#Cc1cncc(-c2ccc3c(c2)[C@@]2(N=C(C)C(N)=N2)[C@]2(CC[C@@H](OC)CC2)C3)c1]

CNP520/umibecestat available, for example, from Medkoo Biosciences, Inc., Morrisville, NC)

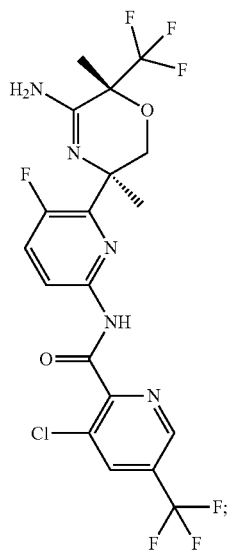 [SMILES: C[C@@]1(c2nc(NC(=O)c3ncc(C(F)(F)F)cc3Cl)ccc2F)CO[C@@](C)(C(F)(F)F)C(N)=N1]

Elenbecestat (available, for example, from Medkoo Biosciences, Inc., Morrisville, NC)

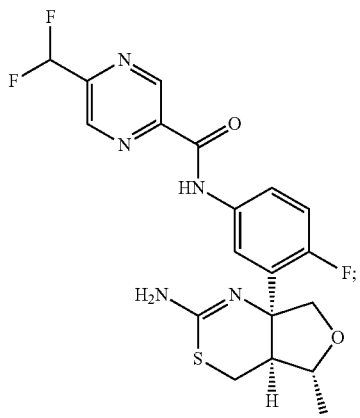 [SMILES: C[C@H]1OC[C@]2(c3cc(NC(=O)c4cnc(C(F)F)cn4)ccc3F)N=C(N)SC[C@H]12]

Atabecestat (JNJ-54861911) (available, for example, from Medkoo Biosciences, Inc., Morrisville, NC)

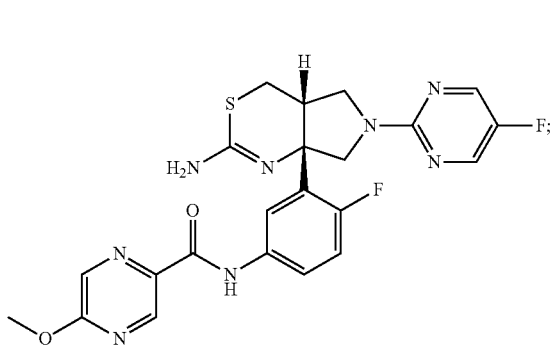 [SMILES: COc1cnc(C(=O)Nc2ccc(F)c([C@]34CN(c5ncc(F)cn5)C[C@H]3CSC(N)=N4)c2)cn1]

LY3202626 (available, for example, from Medkoo Biosciences, Inc., Morrisville, NC)

AZD3839 (available, for example, from Selleckchem (Houston, TX)

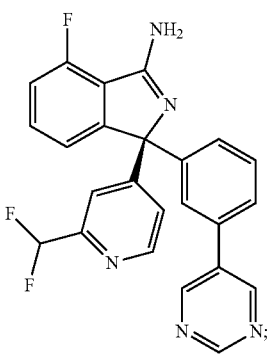 [SMILES: NC1=N[C@@](c2cccc(-c3cncnc3)c2)(c2ccnc(C(F)F)c2)c2cccc(F)c21]

pharmaceutically acceptable salts thereof, and/or combinations thereof.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC (CH2)n COOH where n is 0 4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Similarly, any suitable mGluR agonists may be used, such as those that enhance synaptic plasticity. In one non-limiting embodiment, the mGlu agonist includes, but is not limited to an mGluR1 agonist, an mGluR5 agonist, and/or an mGluR7 agonist. In other non-limiting embodiments, the mGluR agonist may comprise:

(RS)-2-Chloro-5-hydroxyphenylglycine (CHPG; TOCRIS), and/or N-[3-Chloro-4-[(5-chloro-2-pyridinyl)oxy] phenyl]-2-pyridinecarboxamide (VU 0422288; (available, for example, from Tocris Biosciences, Minneapolis, MN);

(S)-3,5-dihydroxyphenylglycine (DHPG); (R,S)-3,5-dihydroxyphenylglycine, quisqualate, trans-azetidine-2,3-dicarboxylic acid, 3-hydroxyphenylglycine (available, for example, from Tocris Biosciences, Minneapolis, MN);

VU6000799 (available from, for example, Synblock, Montreal):

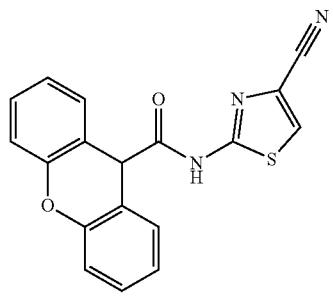 [SMILES: N#Cc1csc(NC(=O)C2c3ccccc3Oc3ccccc32)n1]

VU6000790 (see, for example, Bioorg Med Chem Lett. 2016 May 1; 26(9): 2289-2292. doi:10.1016/j.bmcl.2016.03.044):

ACPT1 (available, for example, from Medkoo Biosciences, Inc., Morrisville, NC):

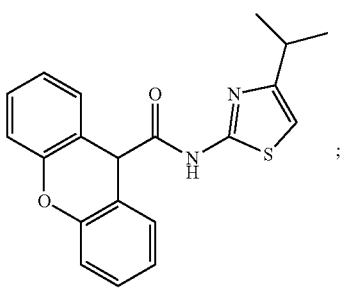 [SMILES: CC(C)c1csc(NC(=O)C2c3ccccc3Oc3ccccc32)n1]

(R,S)-PPG (available, for example, from Tocris Biosciences, Minneapolis, MN):

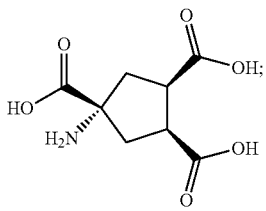 [SMILES: N[C@@]1(C(=O)O)C[C@H](C(=O)O)[C@H](C(=O)O)C1]

Ro 67-7476 ((2S)-2-(4-Fluorophenyl)-1-[(4-methylphenyl)sulfonyl]-pyrrolidine) (available, for example, from Tocris Biosciences, Minneapolis, MN):

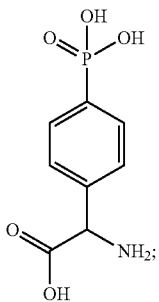

Ro0711401 N-[4-(trifluoromethyl)-1,3-oxazol-2-yl]-9H-xanthene-9-carboxamide (available, for example, from Medkoo Biosciences, Inc., Morrisville, NC):

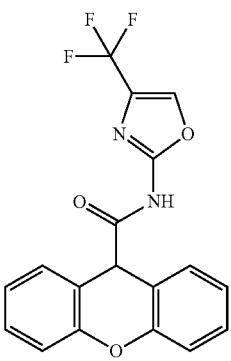

pharmaceutically acceptable salts thereof, and/or combinations thereof.

The BACE1 inhibitor; and the mGluR agonist may be administered together or sequentially. If administered sequentially they can be administered one immediately after the other or after the passage of any amount of time deemed suitable by attending medical personnel.

The subject may be any mammal that has Alzheimer's disease (AD), Down's syndrome, Parkinson's disease, vascular dementia, Dementia with Lewy Bodies, and/or frontal temporal dementia. In one embodiment, the subject is a human.

In another embodiment, the subject, such as a human subject, possesses an apolipoprotein E (APOE) ε4 allele. The APOE ε4 allele is the major known risk-factor gene for late-onset Alzheimer's disease. Human population carrying ApoE ε4 allele have a higher chance to develop AD in their late ages. Other AD early onset patients carrying APP, PS1 mutations will be targeted. People having certain Trem2 mutation or others will develop AD in higher chances. The common feature of these mutations is causing increased Amyloid deposition. In various further embodiments, the subject, such as a human subject, possesses mutations associated with AD disease incidence and/or progression in one or more of an amyloid precursor protein (APP) gene, a presenilin 1 (PS1) gene, and/or a Trem 2 gene.

Dosage levels of the order of from about 0.1 mg to about 500 mg per kilogram of body weight per day are useful in the treatment of the above-indicated conditions. The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day.

It will be understood, however, that the specific dose level for any particular subject will depend upon a variety of factors including the activity of the specific compound employed, the age, body weight, general health, sex, diet, time of administration, route of administration, and rate of excretion, drug combination and the severity of the particular disease undergoing therapy.

In another aspect, the disclosure provides pharmaceutical compositions, comprising:
(a) a BACE1 inhibitor; and
(b) an mGluR agonist.

The pharmaceutical compositions can be used, for example, in the therapeutic methods disclosed herein. Any suitable BACE1 inhibitor capable of reducing Aβ levels may be used in the compositions of the disclosure. In one embodiment, the BACE1 inhibitor is selected from the group including but not limited to SCH1682496 (6-(3-chloro-5-(5-prop-1-yn-1-yl)pyridin-3-yl)thiophen-2-yl)-2-imino-3,6-dimethyltetrahydropyrimidin-4(1H)-one); LY2811376, verubecestat, lanabecestat, umibecestat, elenbecestat, atabecestat, LY3202626, AZD3839, pharmaceutically acceptable salts thereof, and/or combinations thereof.

Any suitable mGluR agonists may be included in the compositions, such as those that enhance synaptic plasticity. In one embodiment, the mGlu agonist includes, but is not limited to an mGluR1 agonist, an mGluR5 agonist, and/or a mGluR7 agonist. In other embodiments the mGlu agonist includes, but is not limited to, (RS)-2-Chloro-5-hydroxyphenylglycine (CHPG), 3-Chloro-4-[(5-chloro-2-pyridinyl)oxy]phenyl]-2-pyridinecarboxamide (VU 0422288); (S)-3,5-dihydroxyphenylglycine (DHPG); (R,S)-3,5-dihydroxyphenylglycine, quisqualate, trans-azetidine-2,3-dicarboxylic acid, 3-hydroxyphenylglycine; VU6000799, VU6000790, ACPT1, (R,S)-PPG, Ro 67-7476, Ro0711401, pharmaceutically acceptable salts thereof, and/or combinations hereof.

The compounds/compositions described herein may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. The pharmaceutical compositions described herein may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compositions disclosed herein may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredients that may be combined with the carrier materials to produce a single dosage form will vary depending upon the host treated and the particular mode of administration. Dosage unit forms will generally contain between from about 1 mg to about 500 mg of active ingredients. The daily dose can be administered in one to four doses per day It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy. The compositions of the disclosure may be administered alone or in combination with at least one additional therapeutic agent. The compositions of the disclosure may be combined with one or more additional therapeutic agents simultaneously or sequentially.

In one embodiment, the composition is formulated for oral delivery, intravenous delivery, or intraperitoneal delivery.

EXAMPLES

Abnormal accumulation of β-amyloid peptides (Aβ) in the brain leads to pathological development and cognitive dysfunction in Alzheimer's disease (AD). Inhibition of BACE1, which initiates Aβ production, is therefore being explored to treat AD patients. However, despite showing strong reduction in Aβ generation, BACE1 inhibitors have failed to improve cognitive functions in patients, perhaps attributed to the role of BACE1 in synaptic function. Here we explored molecular targets that could potentially reverse BACE1-mediated synaptic impairment, and showed that metabotropic glutamate receptor-1 (mGluR1) activity was reduced in BACE1-null mice. BACE1-null mice treated with mGluR1 positive allosteric modulators exhibited significantly improved long-term potentiation (LTP) of Schaffer Collateral-CA1 synapses as well as cognitive behaviors. Mice treated with clinically-tested BACE1 inhibitors Verabucestat and Lanabecestat showed severe reduction in hippocampal LTP, and this reduction was either reversed or mitigated when mGluR1 positive allosteric modulators were administrated. Together, our data suggest that a therapy combining BACE1 inhibitors for reducing amyloid deposition and an mGluR positive allosteric modulator for counteracting BACE1-mediated synaptic deficits is a more effective approach for treating AD patients.

BACE1 has been shown to regulate synaptic function as BACE1-null mice exhibit impaired synaptic transmission and plasticity, manifested by reduced long-term potentiation (LTP) in Schaffer collateral-CA1 synapses and in mossy fiber-CA3 synapses. When BACE1 is ablated in adult conditional knockout mice, despite of reversal of pre-existing amyloid plaques, LTP reduction is also reduced. Consistent with this, mice treated with BACE1 inhibitors such as SCH1682496 or LY2811376 also exhibited impaired hippocampal LTP and reduced spine formation in layer V pyramidal neurons. Therefore, global and dramatic inhibition of BACE1 over a long period appears to compromise the benefit of Aβ reduction due to mechanistic side effects associated with synaptic impairment.

To understand the potential cause of synaptic impairment in BACE1-null mice, we explored molecular targets that are altered in BACE1-null mice. We compared a battery of synaptic proteins in synaptosomes and found that reduction of the metabotropic glutamate receptor-1 (mGluR1) was significant in BACE1-null mouse brains. To answer whether enhancing mGluR1 activity will impact synaptic impairments in BACE1-null mice, we treated BACE1-null mice with the specific mGluR1-positive allosteric modulator Ro0711401 (Vieira et al. 2009). Encouragingly, this treatment significantly elevated LTP and improved learning and memory. We noted that two clinically tested BACE1 inhibitors, Verubecestat (MK-8931) and Lanabecestat (AZD3293), showed more severe reduction in LTP than BACE1 deficiency in mice, and this reduction can also be mitigated by Ro0711401. Our results suggest that BACE1 inhibitors should be better used together with mGluR1 positive allosteric modulators for effective treatment of Alzheimer's patients.

Results

BACE1 Deficiency Reduces mGluR1 Expression

Figure 1B:
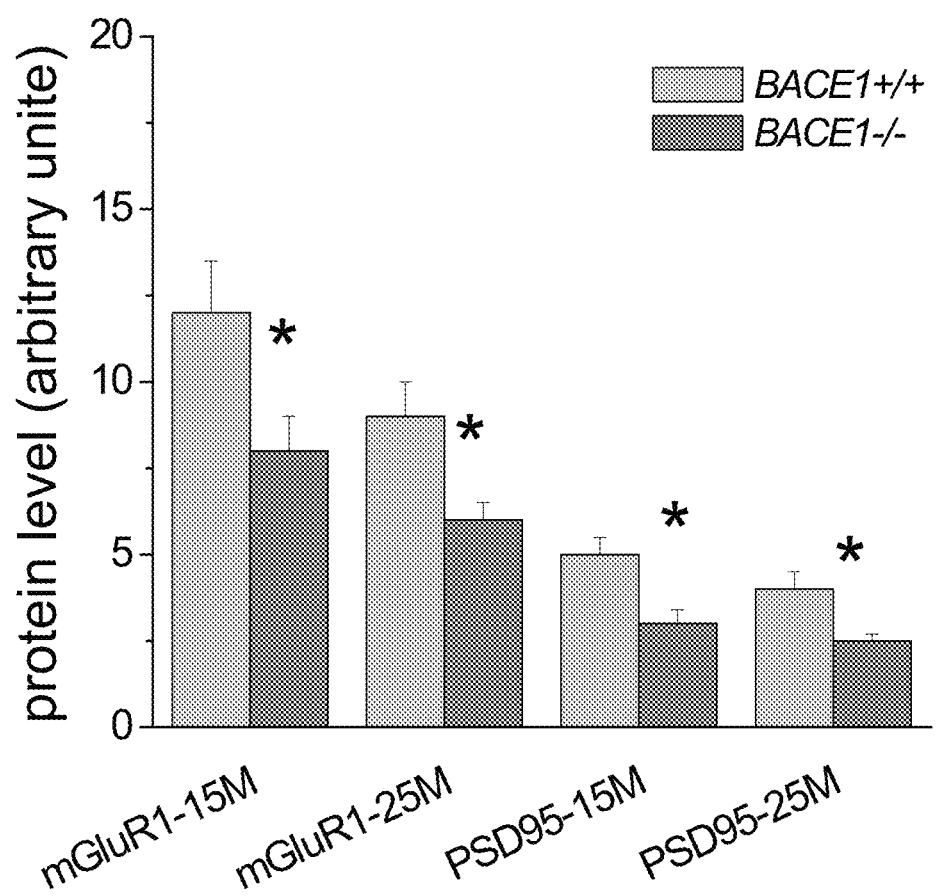
Figure 1C:
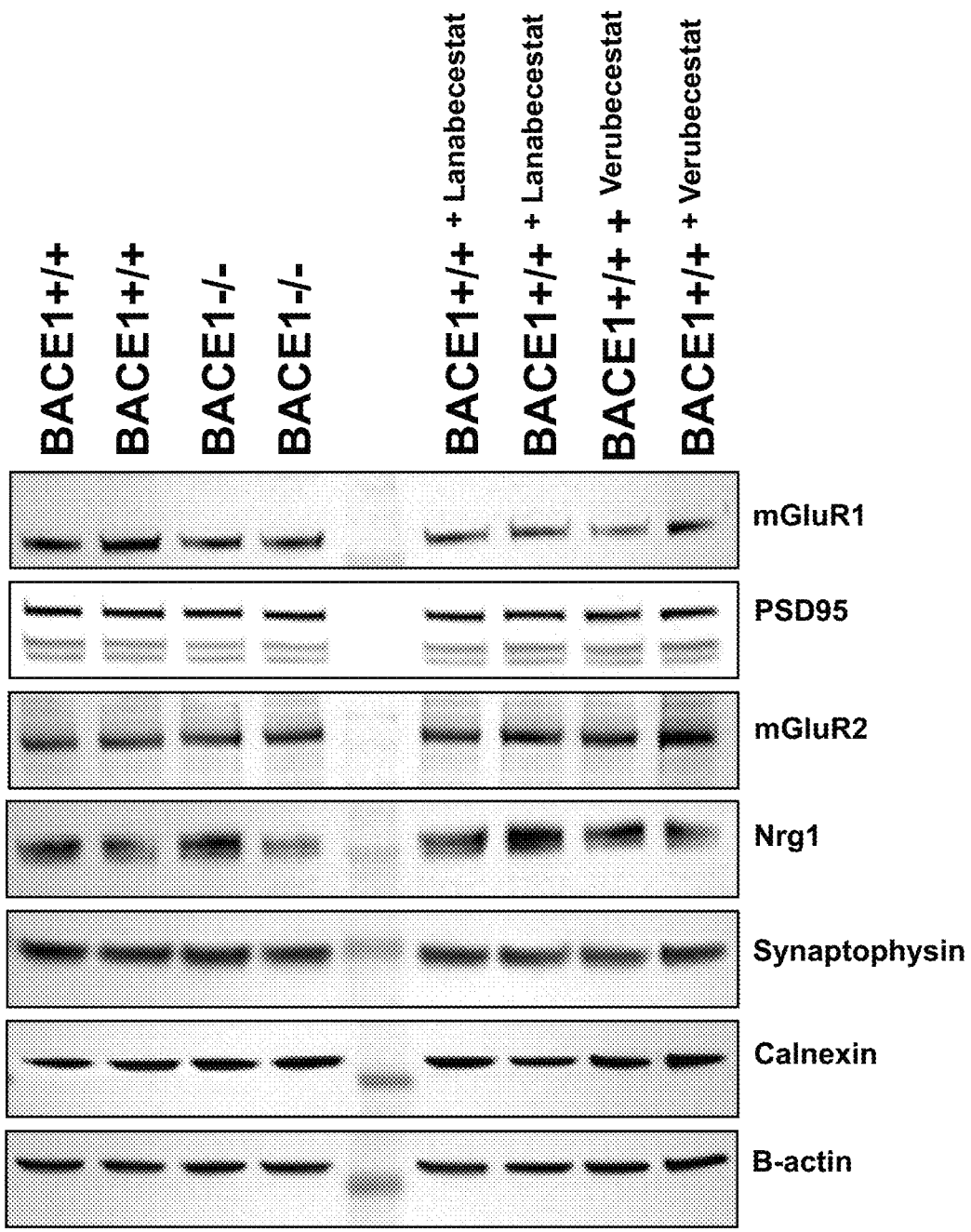
Figure 1D:
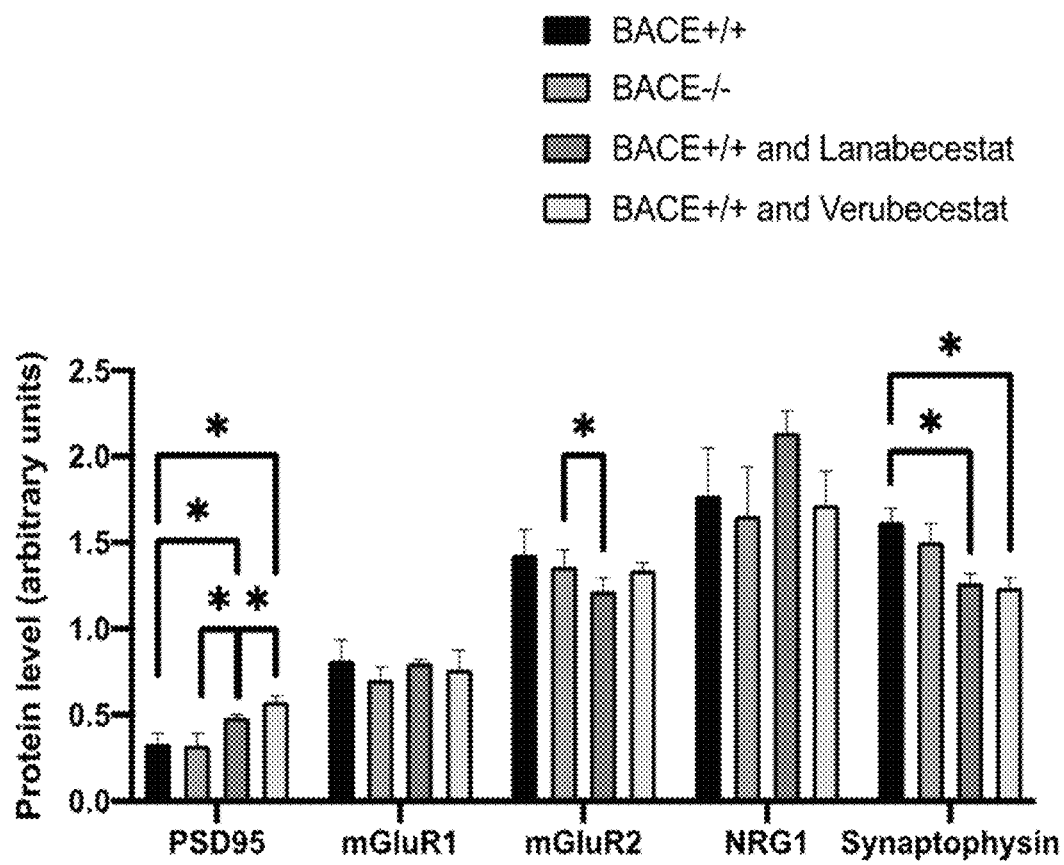

To determine which synaptic molecules contribute to reduced LTP and synaptic plasticity upon BACE1 deficiency or inhibition, we isolated synaptosomes from both WT and BACE1-null mouse brains at different age groups to discern potential changes in synaptic proteins upon BACE1 deficiency. Commercially available antibodies to synaptic proteins were used for western analyses. We noted a reduction of protein levels in glutamate metabotropic receptor 1 (mGluR1) and postsynaptic PSD-95 in both 15-month-old and 25-month-old hippocampi (FIG. 1A), and this reduction was statistically significant when normalized to loading controls (FIG. 1B, N=3 experiments, two pairs each, *P<0.05, Student's t-test). Slight decrease of mGluR5 was seen in 25-month old but not in 15-month old brain samples. No significant changes in protein levels of mGluR2, GluR1, GluR2/3 or GluR4 were observed. It is noted that the expressions of both PSD95 and mGluR1 were age-dependent, and their lower levels are correlated with reduced synaptic function in aging mice (Chapman et al., 1999; Dickstein et al., 2013). NMDAR1 was also lower in 25-month old mouse brains compared to 15-month old mouse brains, but there was no statistical significance between WT and BACE1-null mouse brains. With chronic treatment of BACE1 inhibitors Lanabecestat (AZD3293) and Verubecestat (MK-8931), we also observe significant decrease in PSD95,mGluR2 and Synaptophysin levels ((FIG. 1C,D, N=3 experiments, two pairs each, *P<0.05, Student's t-test).

Potentiation of Group I mGluR Activity Ameliorates Synaptic Impairment in BACE1-Null Mice.

Figure 2A:
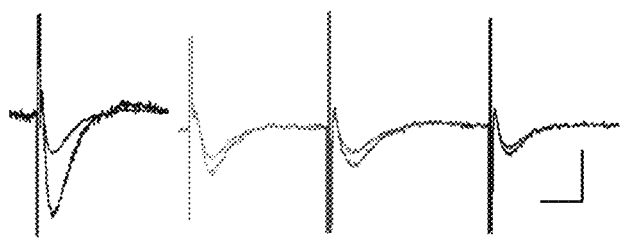
FIG. 2A-2C: BACE1 inhibitors markedly reduce long-term potentiation. (A) LTP was recorded on horizontal hippocampal slices from 4-6-month-old WT (BACE1+/+) mice treated with Lanabecestat (AZD3293) at 0.5 mg/kg or Verubecestat at 3 mg/kg. At 30 minutes post-stimulation, the potentiation for slices treated with 0.5 mg/kg Lanabecestat were 105.6±0.6137% vs control (BACE1+/+) slices at 245.9±0.9864%, while the slices treated with Verubecestat at 3 mg/kg gave an average potentiation of 113.1±1.353%. The scale bars represent y axis: mV [field excitatory postsynaptic potential (fEPSP)] and X axis: ms (time) in all figures. Top panel shows example traces from each category. (B) An enlarged view that shows the differential LTP reduction effect by Lanabecestat and Verubecestat in comparison to BACE1-null mice. (C) Lower dose of Lanabecestat (0.25 mg/kg) showed significantly less reduction on LTP compared to the higher dose (0.5 mg/kg), suggesting a dose dependent reduction in LTP by this compound. N=7 slices (3 animals) for BACE+/+, N=8 slices (3 animals) for WT with Lanabescstat (0.25 mg/kg), N=8 slices (4 animals) for WT with Lanabescstat (0.5 mg/kg). P<0.01, and *P<0.001, ns meaning no significance, Student's t test.
Figure 2A:
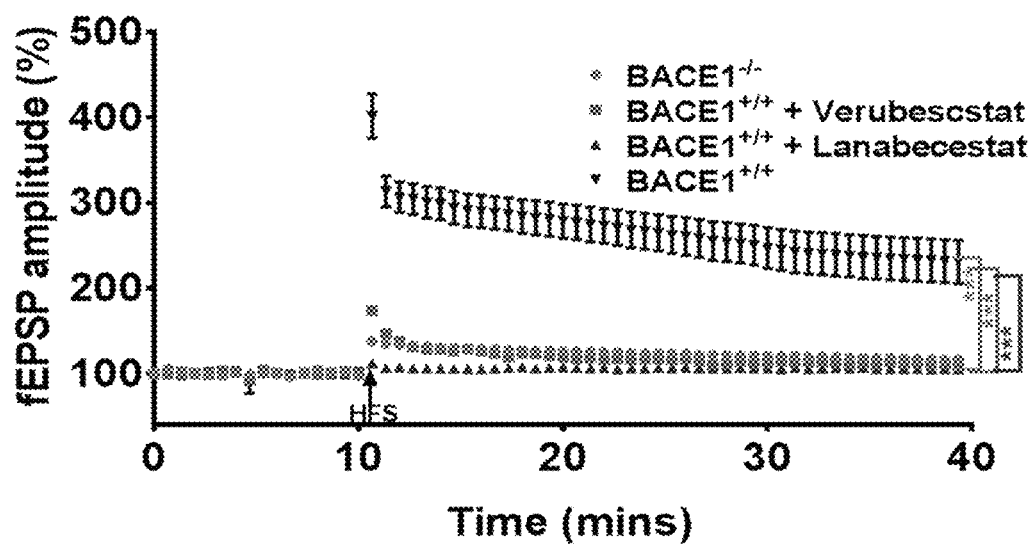
Figure 2B:
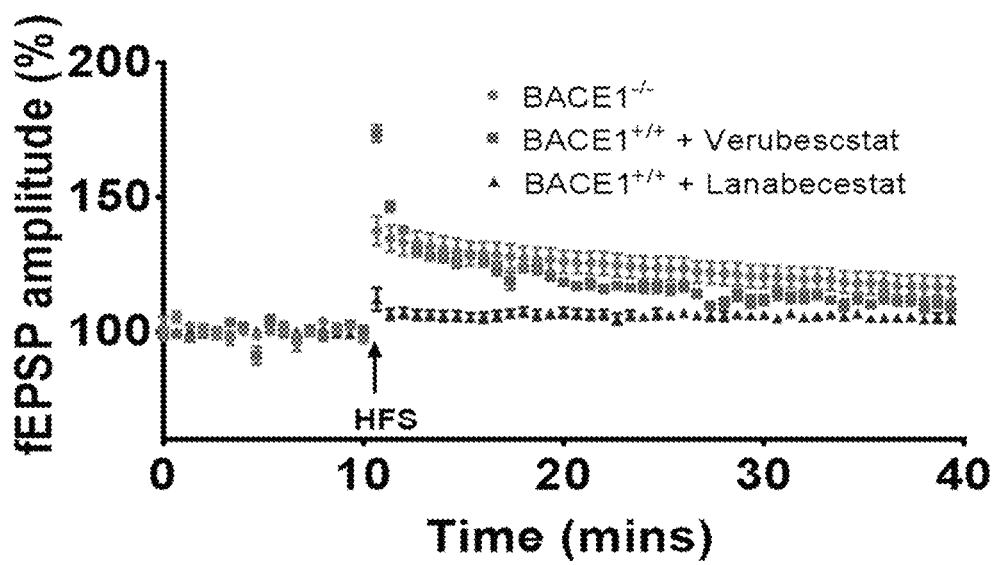
Figure 2C:
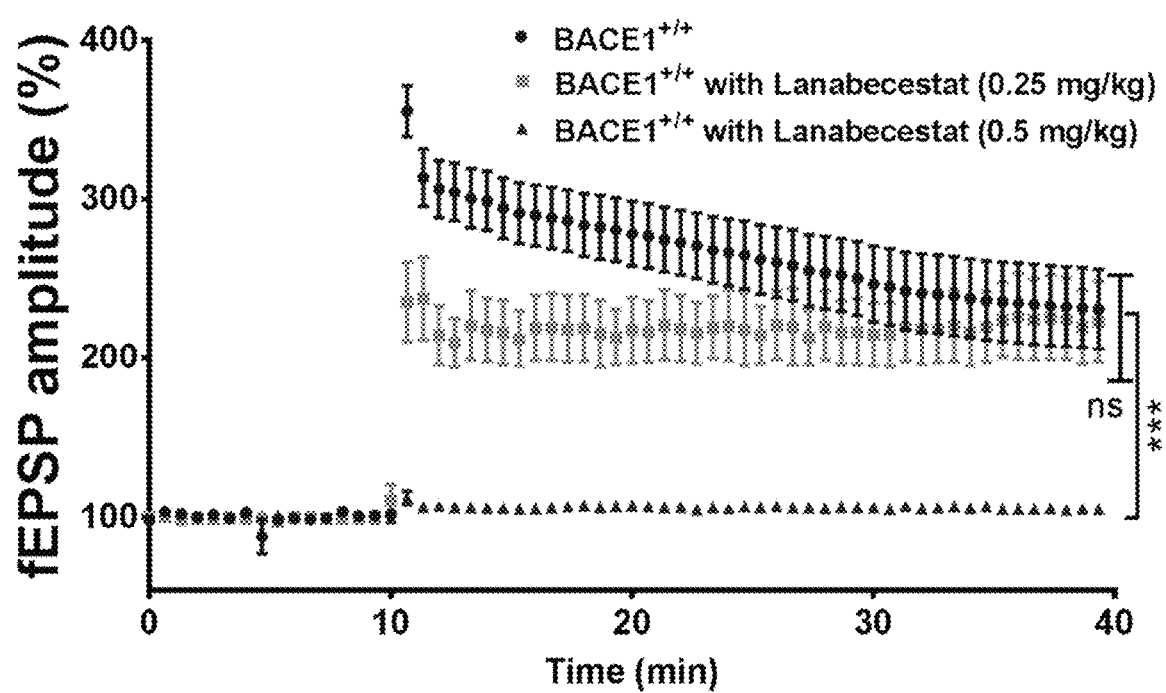

It has been reported previously that BACE1 deletion will causes reduction in LTP. To determine whether brain-penetrable BACE1 inhibitors such as Verubecestat (MK-8931) and Lanabecestat (AZD3293), which are potent in reducing Aβ generation, will affect synaptic plasticity in mice, we treated wild-type (WT, BACE+/+) mice with such compounds over a significant period of time (i.e. at least four months) followed by LTP assays and comparisons. WT mice were treated with either Verubecestat (3 mg/kg) or Lanabecestat (0.5 mg/kg) for 2-4 months beginning at the age of about 2 months. Mice with daily administration of Lanabecestat exhibited strongly suppressed LTP at Schaffer collateral (SC)-CA1 synapses (purple trace in FIG. 2A, N=8, *P<0.001). This reduction appeared to be more severe than that seen in the same age BACE1-null mice (FIG. 2B, circles), suggesting the possible existence of an off-target effect. Mice treated with Verubecestat also exhibited significantly reduced LTP (triangles in FIG. 2A, N=8, *P<0.001), although the detrimental effect was smaller than Lanabecestat, but still worse than that seen in BACE1-null mice (replotted in FIG. 2B for clarity). Impairment was dose dependent as lowering the dose by a half (0.25 mg/kg of Lanabecestat) showed significantly weaker LTP reduction (FIG. 2C).

Figure 3A:
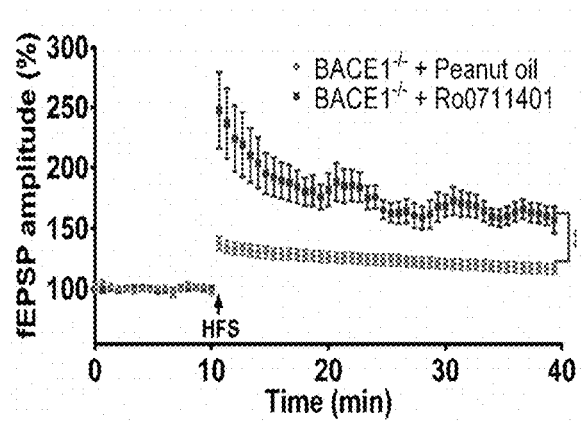
FIG. 3A-3D: mGluR1 positive allosteric modulators improved long term potentiation (LTP) in BACE1-null or inhibited mice. (A) LTP was recorded on horizontal hippocampal slices from 4-6-month-old BACE1-null (KO) mice treated with mGluR1 PAM Ro0711401 at 10 mg/kg injected 1 hour before sacrificing and harvesting acute brain slices. (B) BACE1-null (BACE1−/−) slices were treated with CHPG at 125 nM before high-frequency stimulation during LTP recording, which elicited a significantly improved LTP response when compared to mock treated BACE1-null brain slices. N=8 slices (3 animals) for BACE1 KO, and N=11 slices (3 animals) for BACE1 KO+Ro0711401 and N=10 slices (3 animals) for BACE1 KO with CHPG (, P<0.01, student t-test). (C) CHPG treatment markedly improved LTP in mice treated with Verubecestat at 3 mgl/kg, but less in mice treated with Lanabecestat at 0.5 mg/kg (D). N=8-10 slices in 3-4 animals; , P<0.01; ***, P<0.001; Student's t test.

We postulated that a reduction of mGluR1 contributes to decreased LTP in BACE1-null or -inhibited mice. To test this, we treated 4-6 month old BACE1-null mice with a mGluR1 positive allosteric modulator PAM Ro0711401 (provided by Roche), which is brain-penetrable and has previously been tested in animals (Ngomba et al., 2011; Notartomaso et al., 2013; D'Amore et al., 2014). By following the published protocol (Notartomaso et al., 2013), we intraperitoneally injected 10 mg/kg of Ro0711401 in BACE1-null mice one hour before the animal was sacrificed for LTP recordings. Remarkably, LTP measured from acutely-sectioned brain slices was significantly enhanced compared to BACE1-null mice treated only with vehicle (peanut oil) (FIG. 3A; N=5, **P<0.001, Student's t test), suggesting that acute Ro0711401 treatment rapidly restores LTP levels comparable to mock treatment at SC-CA1 synapses. Both mGluR1 and mGluR5 belong to the group I metabotropic glutamate receptors. We also tested (RS)-2-Chloro-5-hydroxyphenylglycine (CHPG; TOCRIS) (mGluR1 and mGluR5 agonist) in our LTP measurement. Since CHPG is non-brain penetrable, we pre-treated BACE1-null slices with 125 nM CHPG for 30 min followed by LTP measurement. A significantly improved LTP response was also noted (triangles in FIG. 3B). Hence, acutely treated mGluR1 positive allosteric modulators appear to have comparable enhancing effects on LTP in the BACE1-null mouse brain.

Figure 3B:
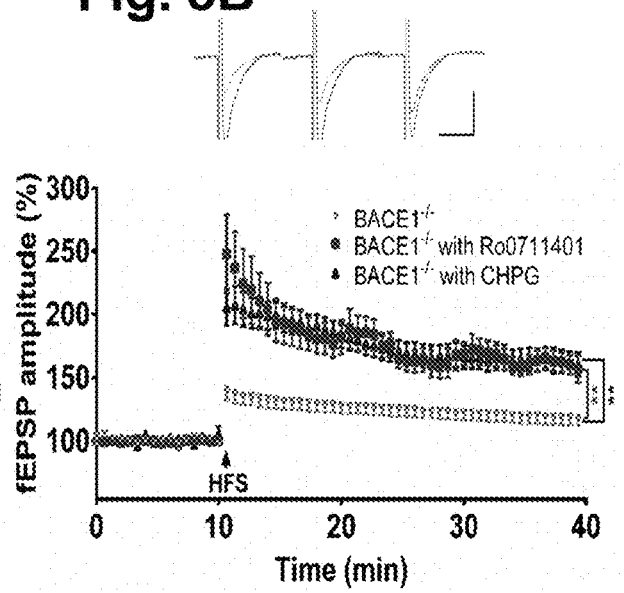
Figure 3C:
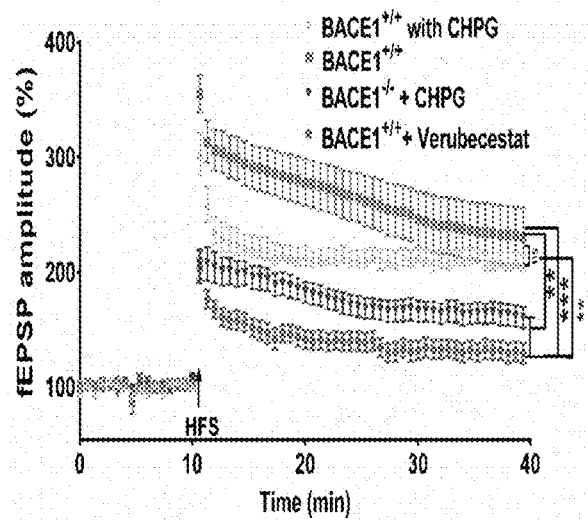
Figure 3D:
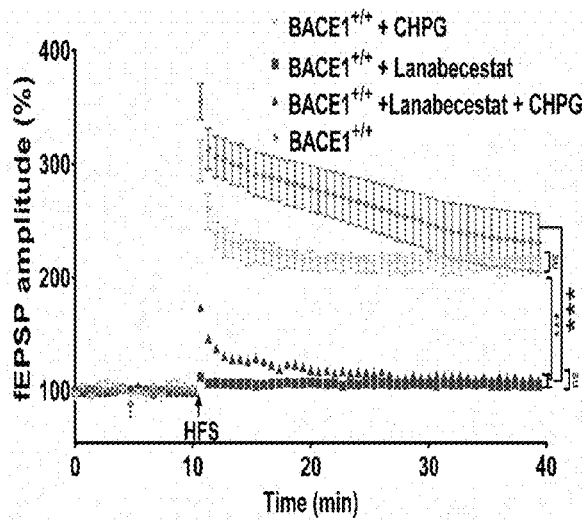

To test whether the reduction of LTP due to BACE1 inhibition would be affected by mGluR potentiation, we treated 4-6 month old WT mice with Verubecestat at 3 mg/kg or Lanabecestat at 0.5 mg/kg for 60 days by oral gavage. For LTP measurements, we bath-treated brain slices with CHPG as described above. Compared to mock treatment, a markedly improved LTP response was noted when CHPG was incubated with brain slices from animals treated with Verubecestat (FIG. 3C, circles 5***P<0.001). Mice treated with Lanabecestat at 0.5 mg/kg exhibited stronger reduction in LTP when compared with Verubecestat at 3 mg/kg in our tests. Mice treated with Lanabecestat and CHPG treatment had a slightly improved LTP responses (FIG. 3D). Hence, mGluR1 positive allosteric modulator significantly mitigates the LTP reduction by Verubecestat treatment and mitigates to a lesser extent the LTP reduction by Lanabecestat treatment in mice.

Improved Psychiatric and Memory Behaviors in BACE1-Null Mice Treated with an mGluR1 Positive Allosteric Modulator We conducted in vivo treatment of BACE1-null mice with Ro0711401 (Roche), which is a brain-penetrable positive allosteric modulator. BACE1-null mice were either given Ro0711401 by intraperitoneal injection at a dose of 10 mg/kg or vehicle (peanut oil) every 12 hours during the testing period, beginning at the age of about 12 months (over a period of 45 days). Both learning behaviors and LTP were examined sequentially in treated mice.

Figure 4A:
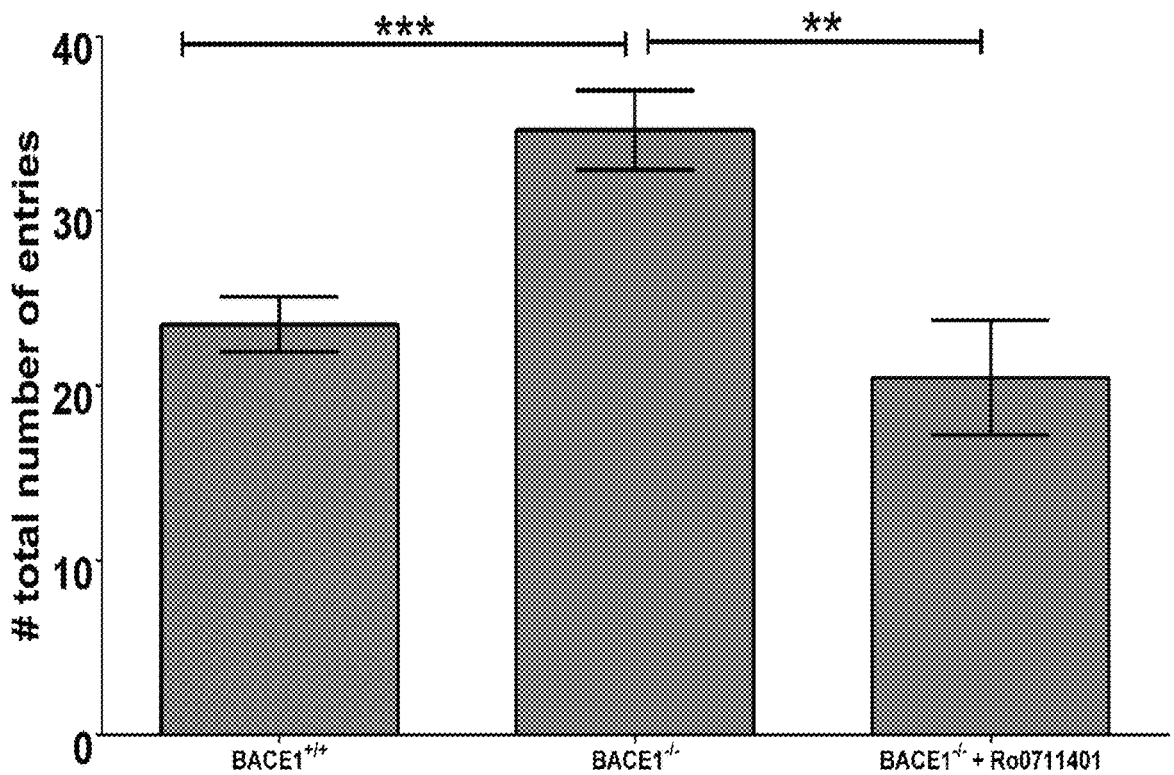
FIG. 4A-4H: Defects in learning and memory in BACE1-null mice rescued by the mGluR1 positive allosteric modulator: (A-B) BACE1-null mice with or without Ro0711401 were first tested on the Y-maze task. Total numbers of arm entry were compared (A), and BACE1-null mice exhibited high numbers of entry. This increase was reverted by Ro0711401 treatment. Changes in percentage of spontaneous alternation were not obvious among three groups. (C-E) BACE1-null mice with or without Ro0711401 were tested in an open field. Significant reversions in the total distance covered (C) and average speed (D) were observed in BACE1-null mice treated with Ro0711401 compared to mock treatment. This decrease suggests a reduction in the anxiety seen in BACE1-null mice. (E) Heat maps showing that mice treated with Ro0711401 explored both the corners and the center of the open field arena similar to WT, while BACE1-null mice spent more time in the corners. (F-J) Mice were tested in the Morris water maze. In the habitation (F) and training (G), BACE1-null mice showed defects in learning, taking much longer time compared to WT and BACE1-null treated with Ro0711401. (H) On day 9 in the Morris water maze test, the number of entries made to the platform quadrant looking for the hidden platform were visibly increased when BACE1-null mice were treated with Ro0711401, and this is more obvious in the representative track plots.
Figure 4B:
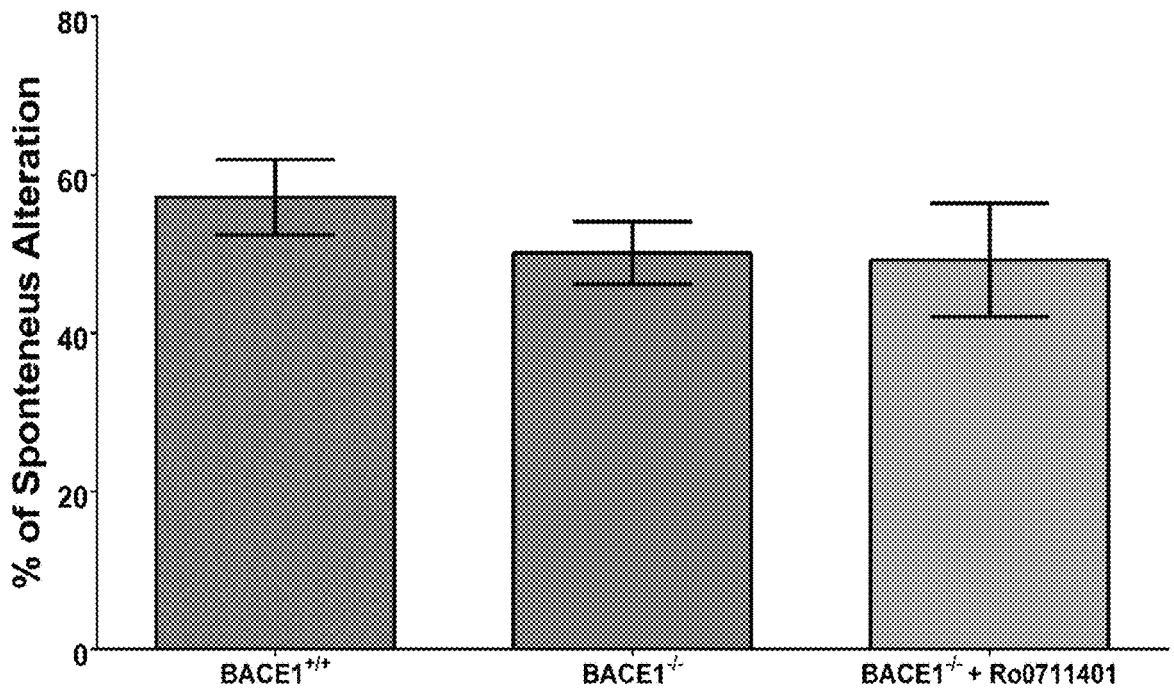

We first conducted Y maze spontaneous alternation task test to evaluate the hippocampus-dependent learning behaviors. BACE1-null mice clearly showed increased total numbers of arm entries, which reflected more active exploratory behaviors (FIG. 4A), likely related to schizophrenia-like behaviors. Remarkably, there was an improved entrance performance in BACE1-null mice treated with Ro0711401 for about 45 days. Spontaneous alternations in the Y-maze was slightly reduced in BACE1-null mice (FIG. 3B).

Figure 4C:
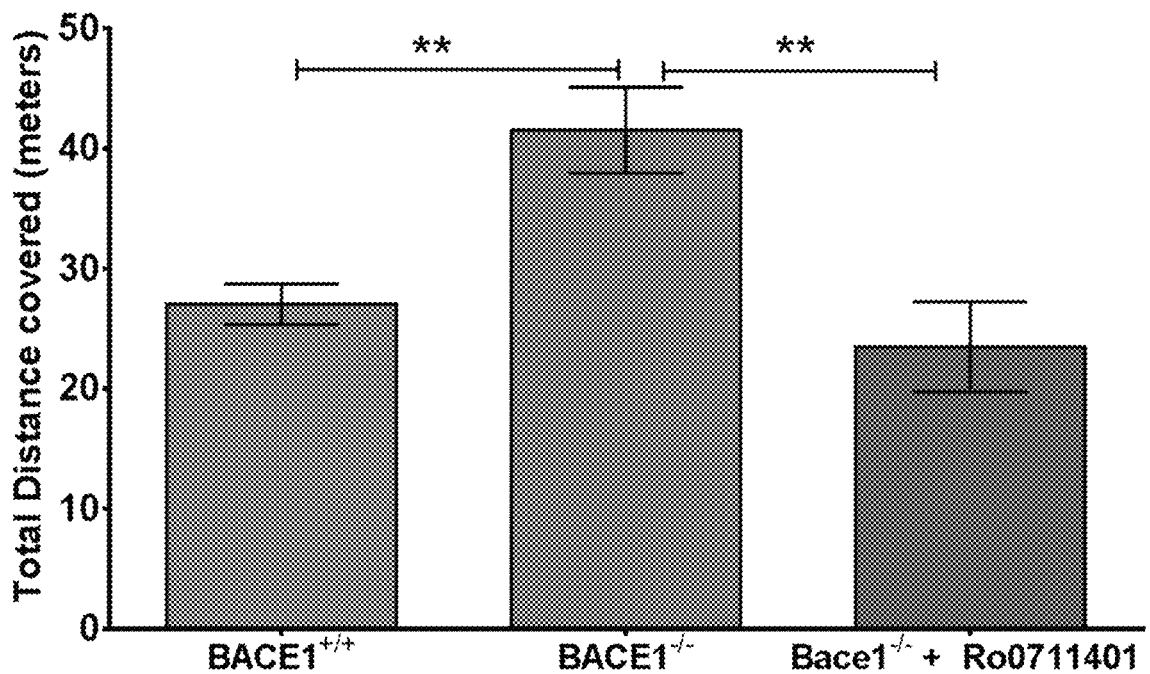
Figure 4D:
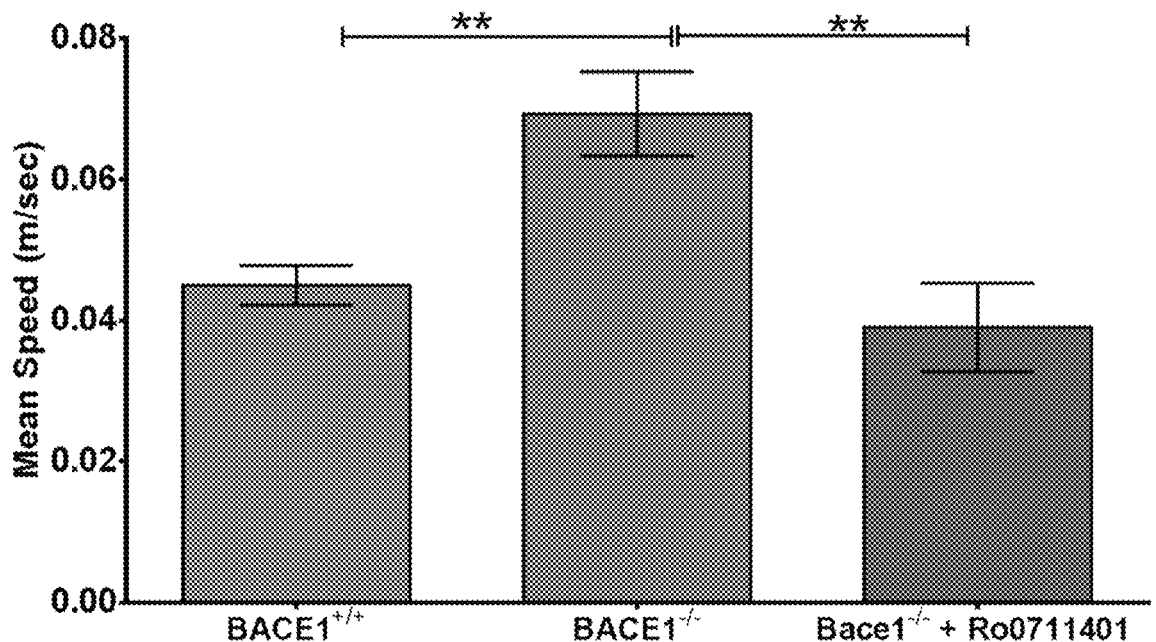
Figure 4E:
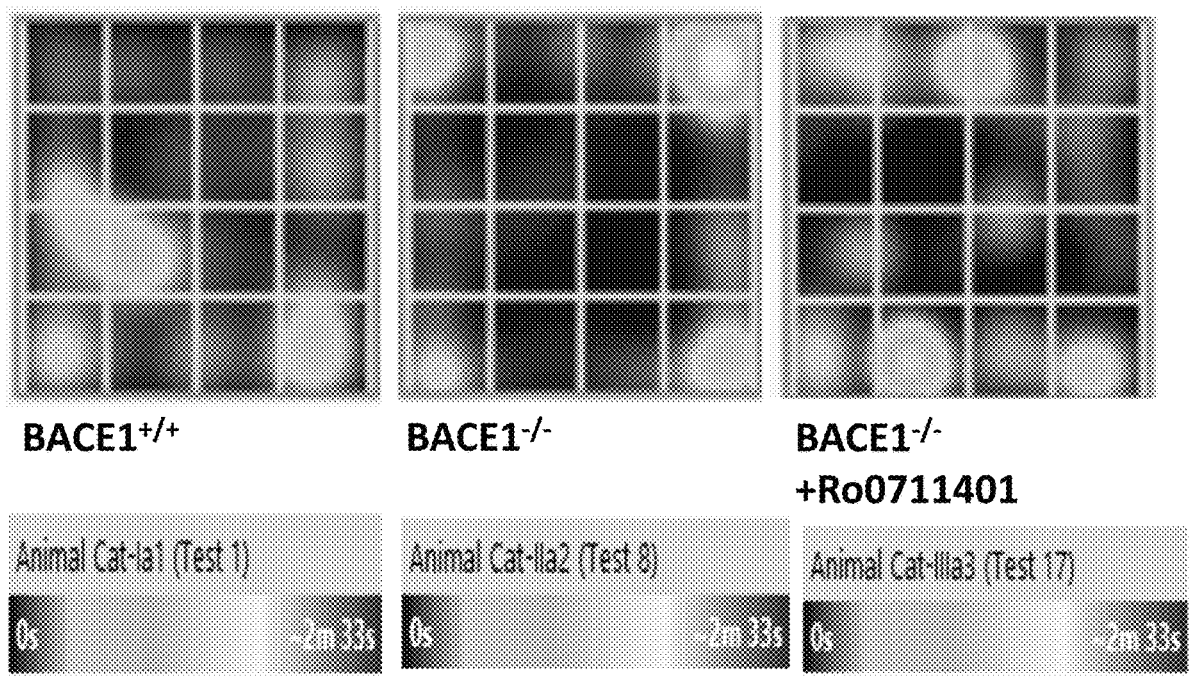
Figure 4F:
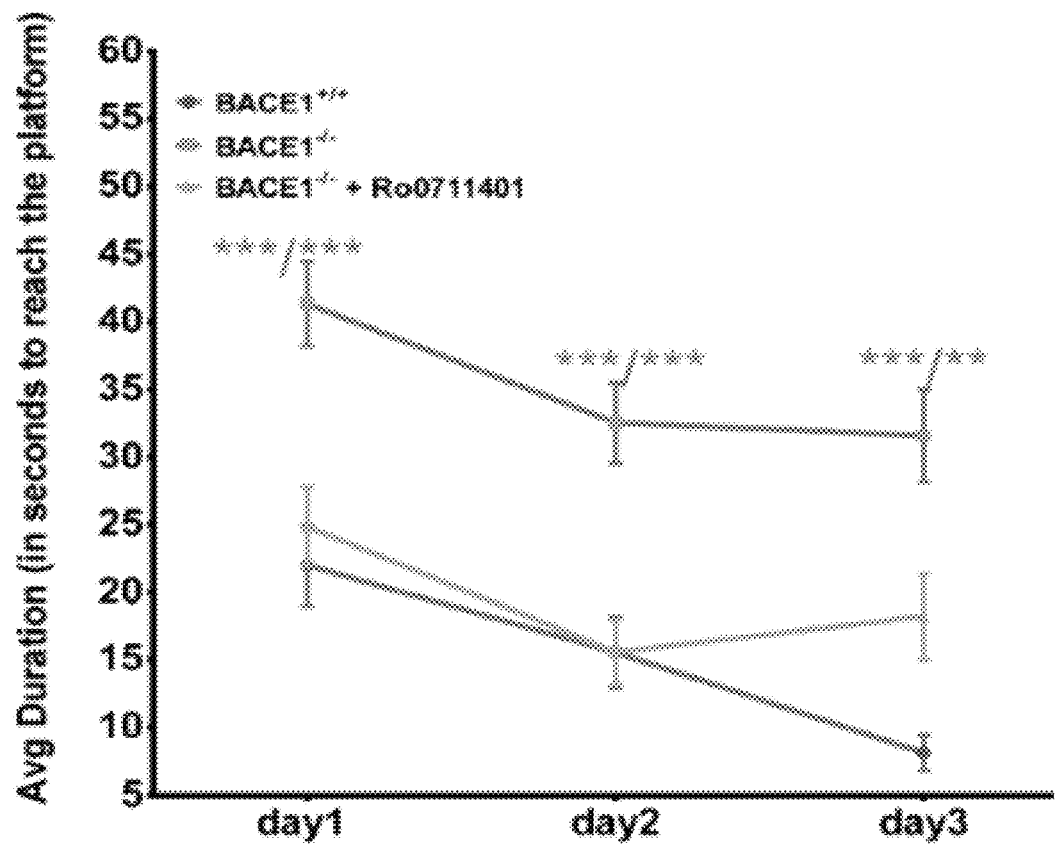

We then conducted the open field test to further assess the impact of the drug on exploratory behaviors associated with BACE1 deficiency. BACE1-null mice significantly traveled longer distances and moved with a faster speed when compared to their WT counterparts (FIG. 4C-D; N=12, P<0.001, Student's t test). After treatment with Ro0711401, the total distance covered by the treated mice in the open field arena was lowered along with their average speed (FIG. 4C-D; N=12, P<0.001, Student's t-test). In addition, we noted that BACE1-null mice were mostly running along the corners and spent much less time in the central space in the open field arena when compared to WT mice (FIG. 4E; N=12, *P<0.05, Student's t test). BACE1-null mice were visibly shown to spend more time spent in the center after the treatment. This observation suggests that application of Ro0711401 can modulate this anxiety behavior in BACE1-null mice.

Figure 4G:
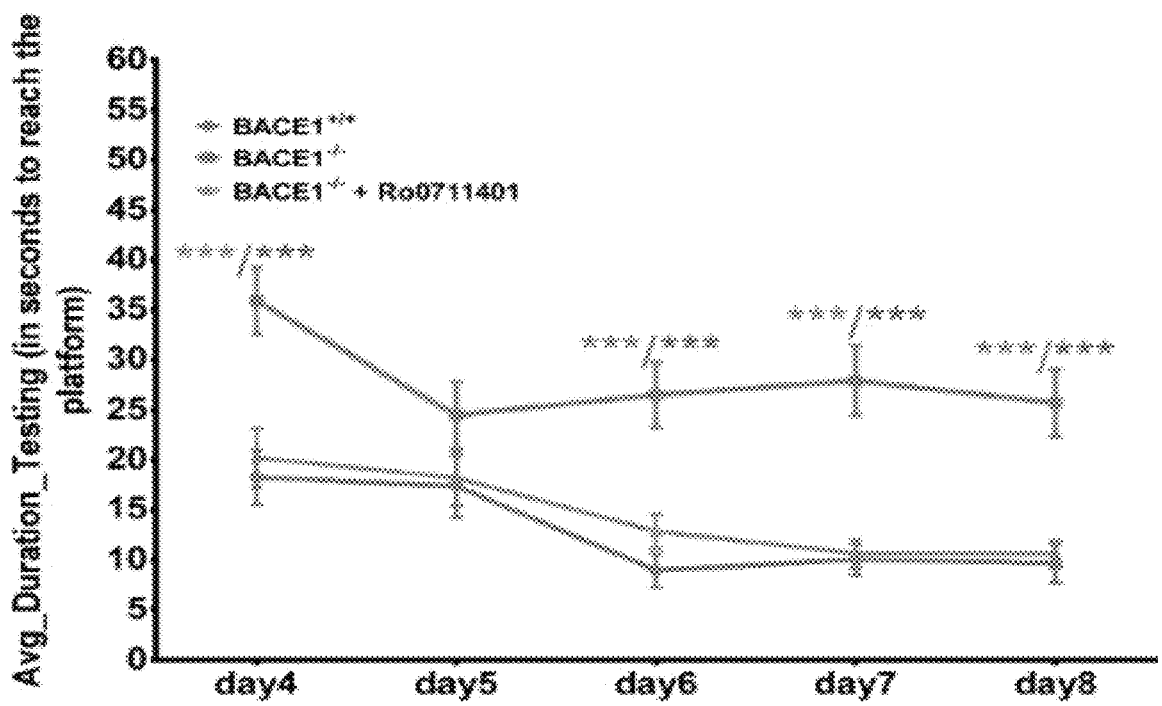

In order to evaluate effects on spatial memory, we also performed water maze experiments. In Morris water maze experiments, spatial learning and memory for mice relies on distal cues to navigate from start locations around the perimeter of an open swimming arena to locate a submerged escape platform. Spatial learning is assessed across repeated trials and reference memory is determined by preference for the platform quadrant of the maze when the platform is absent (Vorhees 2006). WT and BACE1-null mice with or without Ro071141 treatment were habituated in the water maze for three days over four separate trials on each day. BACE1-null mice took a longer time to learn to reach the platform (FIG. 3F; 41.32±3.131 s on day 1 and 31.56±3.432 s on day 3) when compared with WT (21.99±2.986 s on day 1 and 8.098±1.318 s on day 3). BACE1-null mice treated with Ro0711401 showed clear improvement (24.88±2.935 s and 18.20±3.203 s in BACE1-null+Ro0711401 mice, N=12, *P<0.001). Over the next 5 days, the platform was submerged in water and the primary cue (flag attached to the platform) was removed. During this training phase, we again observed that the average duration to reach the platform for BACE1-null mice was significantly higher than the WT and the BACE1-null mice treated with Ro0711401 over all trial days (FIG. 4G; N=12, *P<0.001, Student's t test).

Figure 4H:
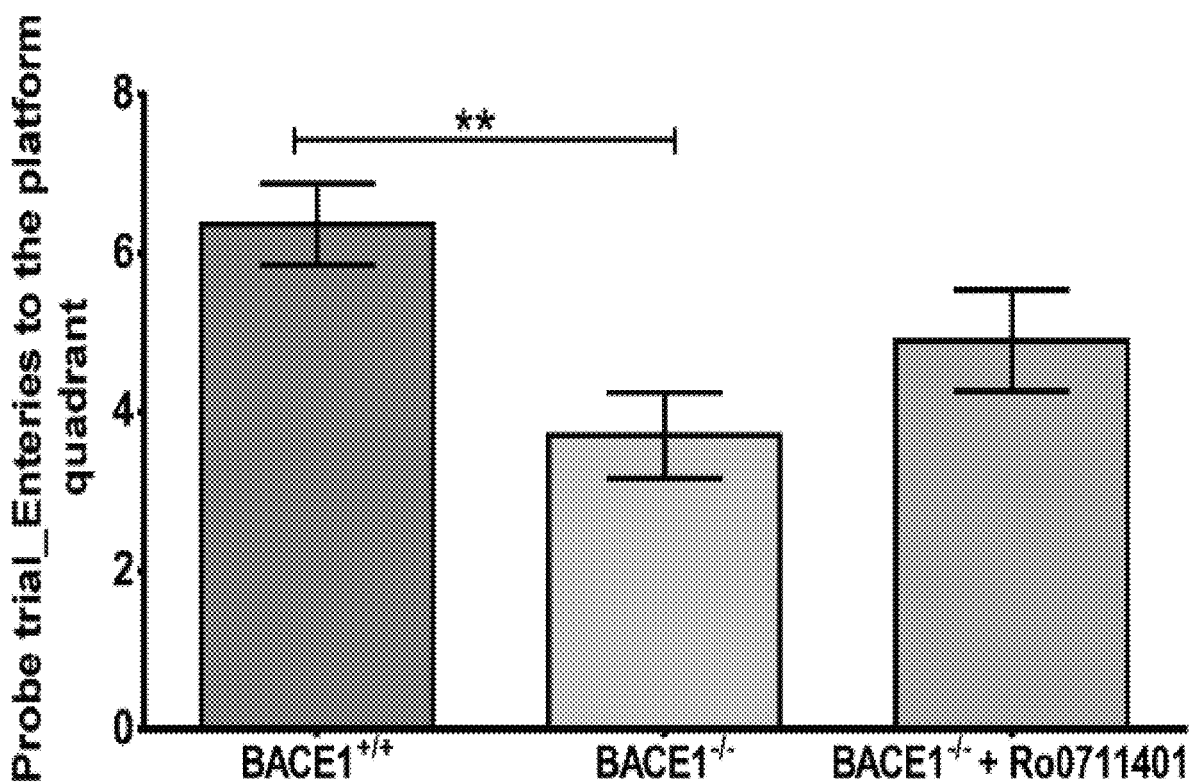

On the 9th day, the platform was removed and the mice were left in the water maze for 60 seconds for testing probe capability. Ro0711401 treatment improved the number of entries made to the platform quadrant compared to BACE1-null mice (FIG. 4H, 6.364±0.5094 in WT vs 3.700±0.5385 in BACE1-null vs 4.900±0.6403 in Ro0711401-treated group, **P<0.001, N=12 each student t-test). We also analyzed swimming behaviors, which were manifested by track plots. The plot visibly showed improved learning behaviors in mice treated with Ro0711401 in reaching platform (FIG. 4I). Moreover, the average distance the animals commuted to reach the platform during the habituation and the training phases was analyzed. The average distance covered over the trials by BACE1-null mice was longest (3.872±0.7645 meters); WT mice, on the contrary, traveled only 1.205±0.2805 meters while BACE1-null mice with Ro0711401 treatment traveled 1.909±0.3878 meters (FIG. 4, N=12; ***P<0.001 between WT and BACE1-/- and * P<0.05 between BACE1-/- and BACE1-/-+Ro0711401; Student's t test), showing improvement in learning to reach the platform at the end of training phase. Collectively, we showed that Ro0711401 treatment in BACE1-null mice improved behaviors in open field and water maze tests.

Figure 5A:
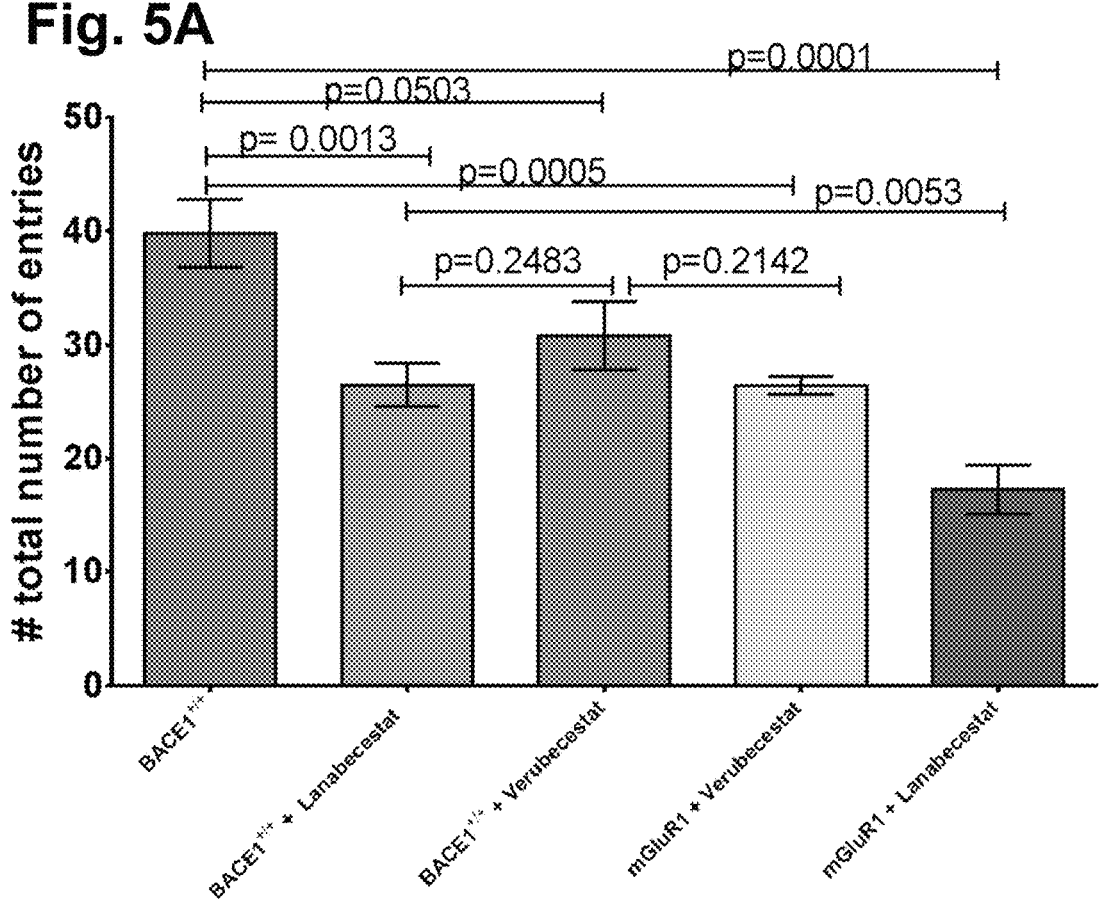
FIG. 5A-5E: BACE1 inhibition in mice impaired learning behaviors are partially rescued by the mGluR1 positive allosteric modulator: Administration of mGluR1 PAM Ro67-7476 improved the number of % spontaneous alteration in Y maze task when given in combination with BACE1 inhibitors Lanabecestat or Verubecestat alone (B) although the number of total entries was markedly reduced (A). We also notice a marked rediuction in the total distance covered and average speed in the open field tasks in the combined treatment group of mgluR1 PAMs and BACE1 inhibitors vs only BACE1 inhibitors. (C,D). (E) Shows the heat maps of animal in open fields task, with BACE1+/+, BACE1+/++ Lanabecestat, BACE1+/++Verubecestat, BACE1+/++ Lanabecestat+Ro67-7476, BACE1+/++Verubecestat+Ro67-7476; , P<0.01; *, P<0.01; Student's t test. Values are expressed as mean±SEM.
Figure 5B:
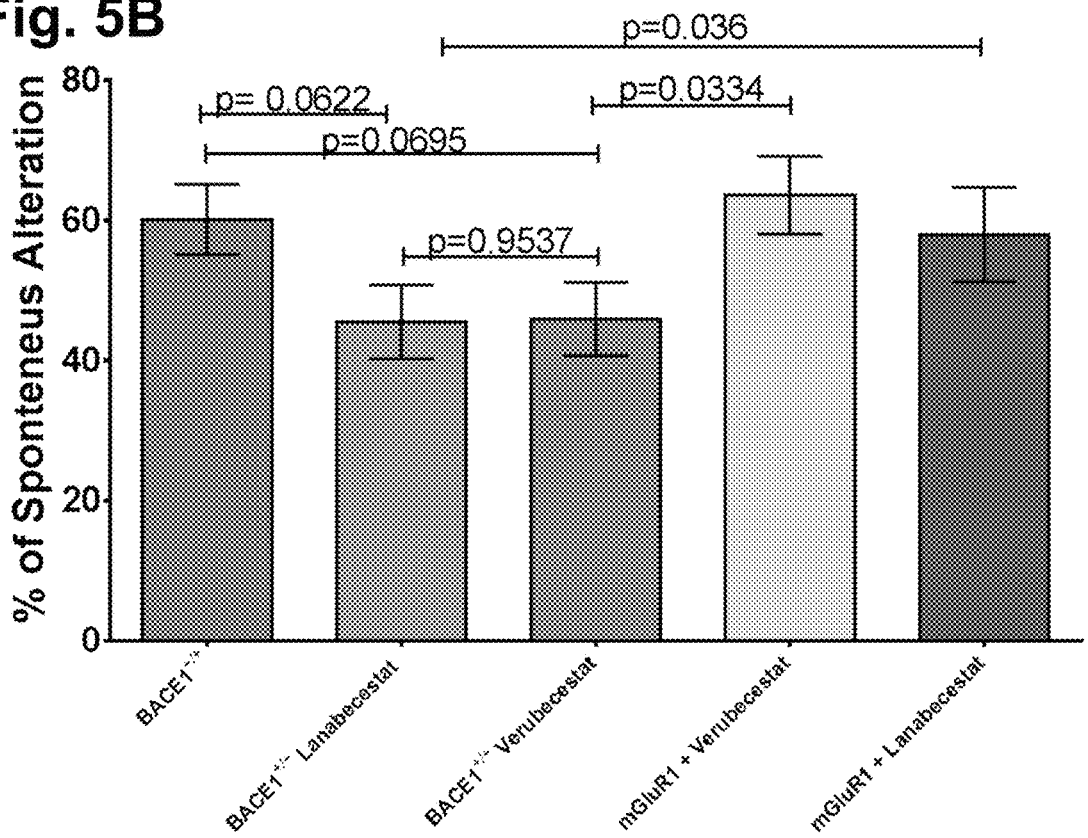
Figure 5C:
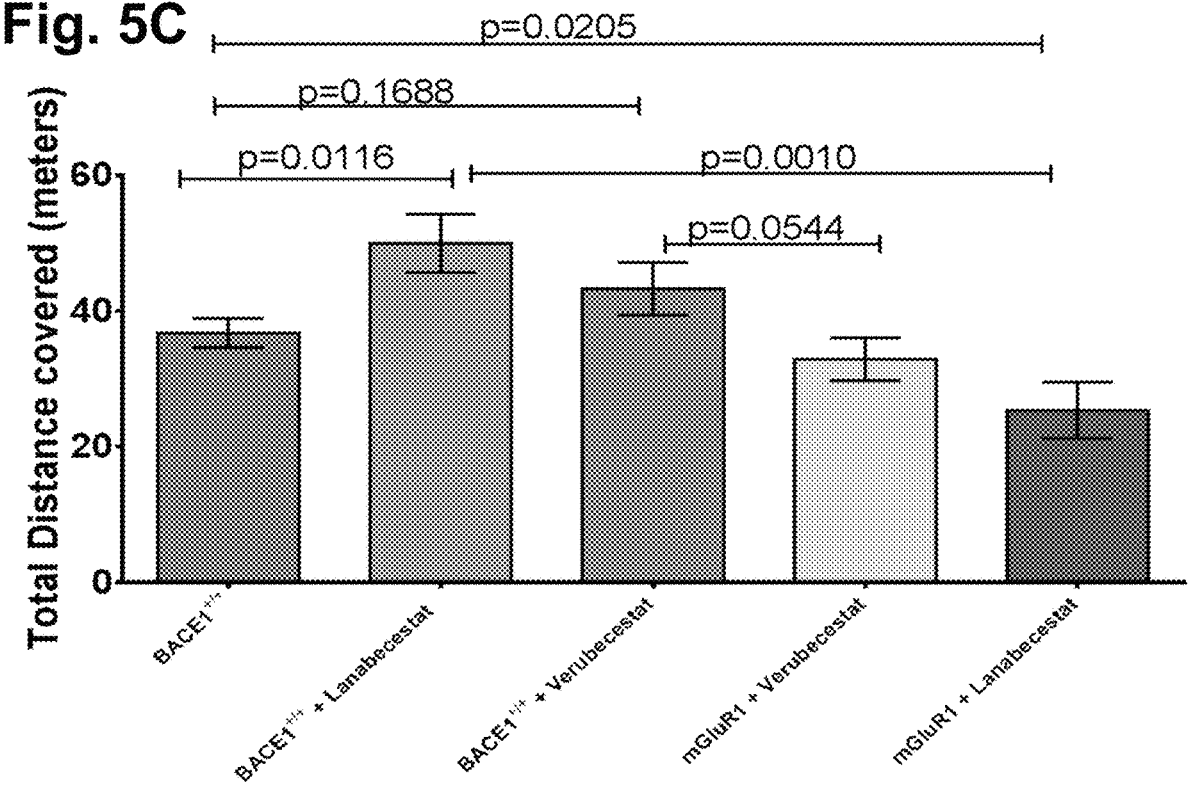
Figure 5D:
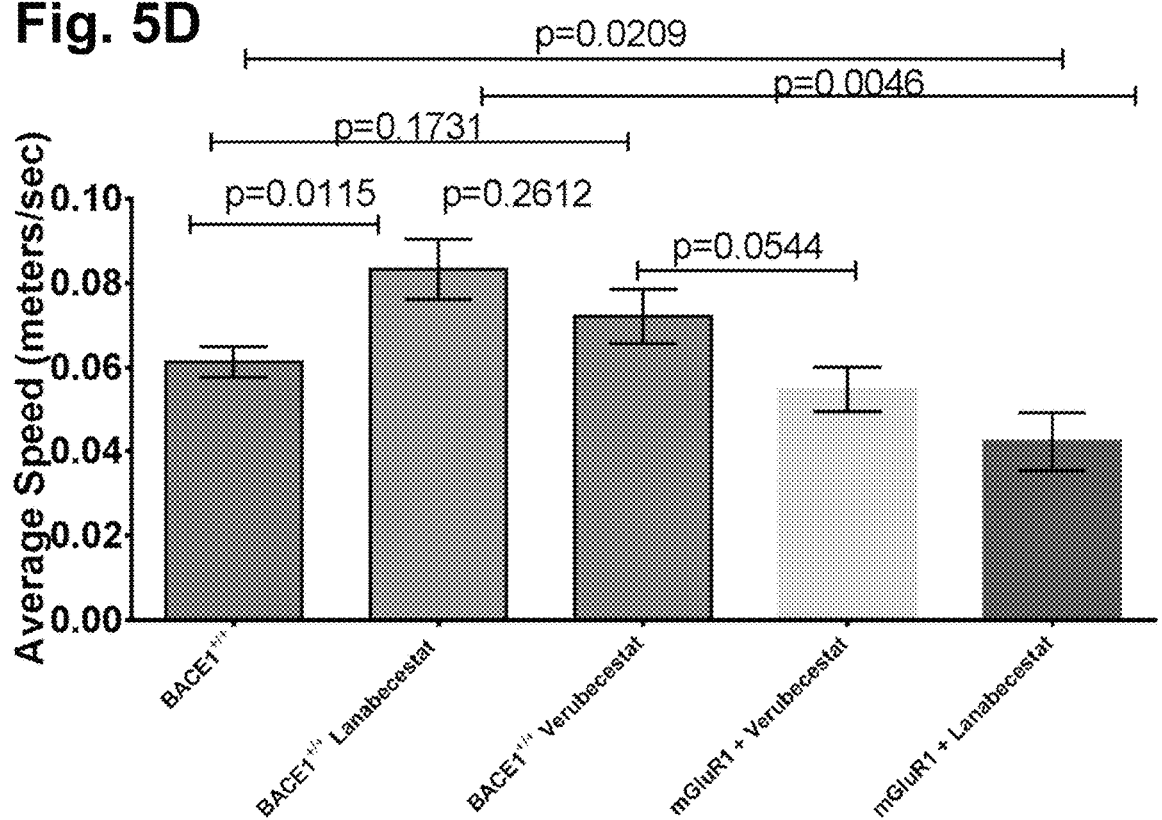
Figure 5E:
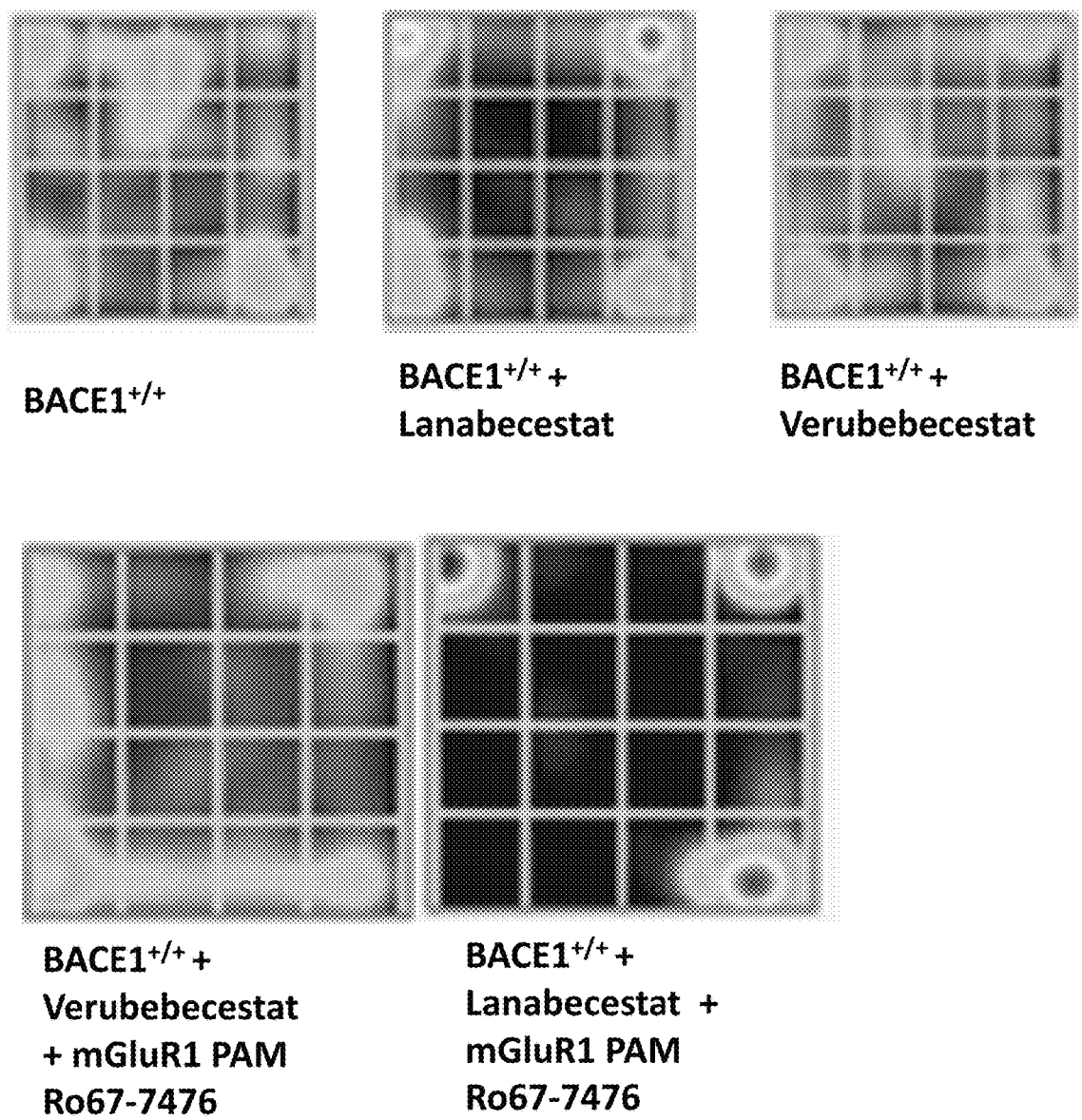
Figure 6A:
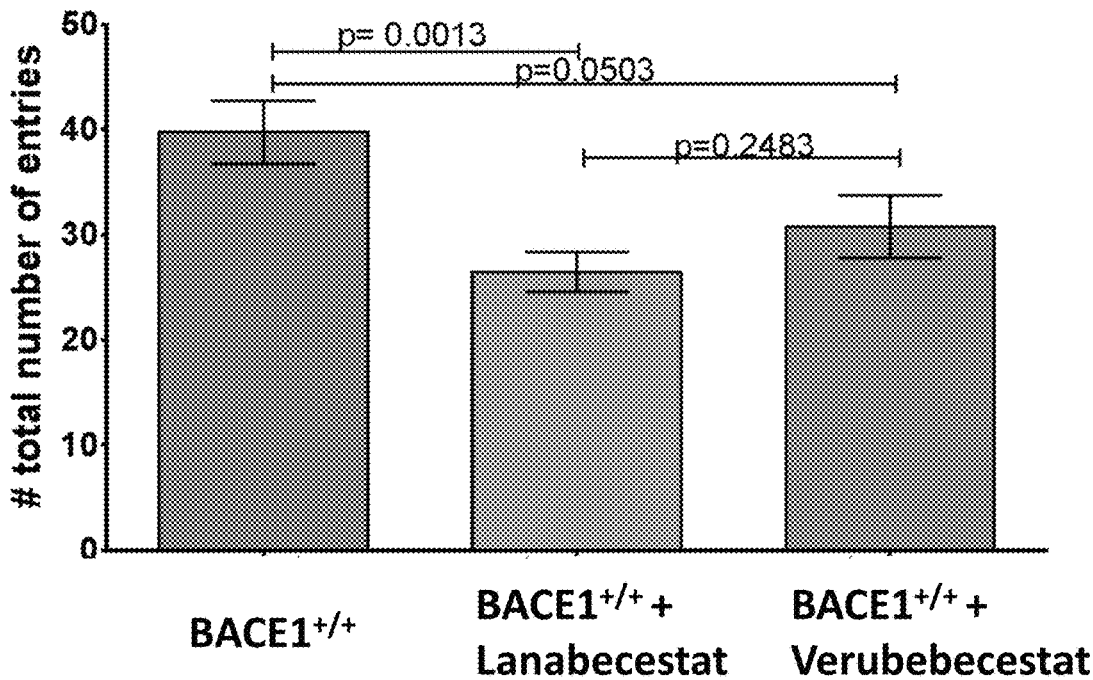
FIG. 6A-6F: BACE1 inhibitors caused impairments in learning and memory behaviors. WT (BACE1+/+) mice treated with Lanabecestat (AZD3293) at 0.5 mg/kg or with Verubecestat at 3 mg/kg for ~2 months were tested for their motor and learning behaviors. (A-B) In Y-maze tests, the number of arm entries and spontaneous alternations in mice treated with Lanabecestat or Verubecestat were clearly reduced. (C-E) In the open field tests, mice treated with BACE1 inhibitor Lanabecestat exhibited less exploratory behaviors with more time spent in the corners compared to the center when compared with mice treated with Verubecestat, which was worse than WT (see heat map in C). (D,E) Lanabecestat-treated mice also showed a clear increase in the total distance covered and speed. (F) Fear conditioning studies in mice treated with Lanabecestat at 0.5 mg/kg or Verubecestat at 3 mg/kg also showed a significant reduction in freezing time in both contextual and cue phases (N=10 in each group, ***P<0.01, Student's t test).
Figure 6B:
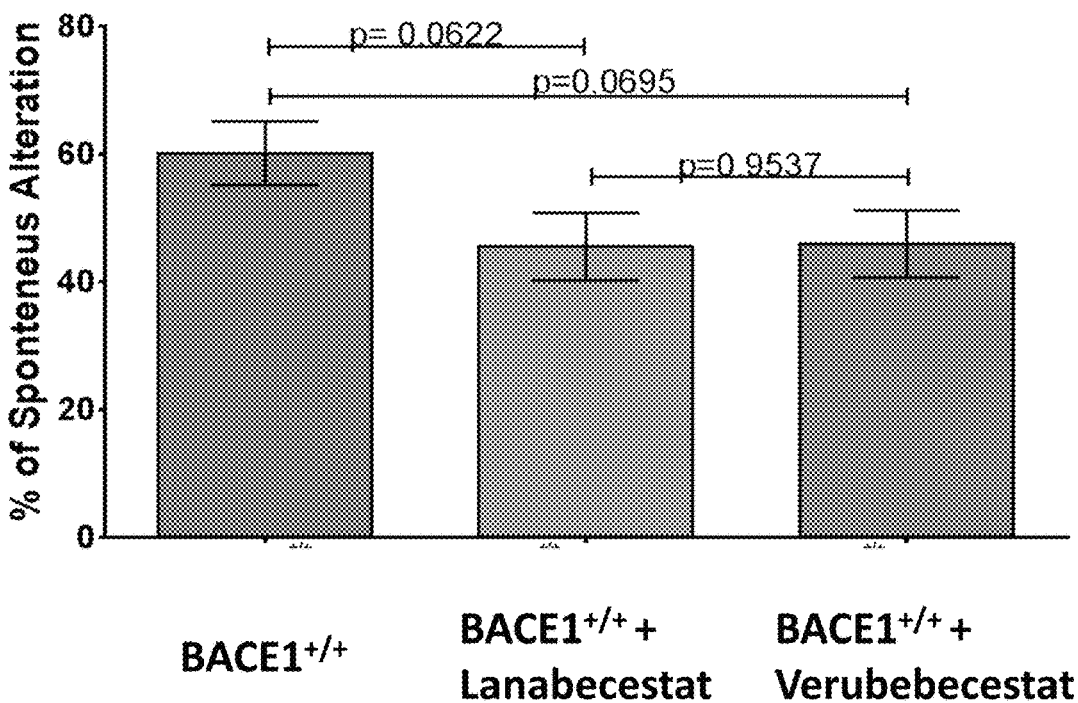
Figure 6C:
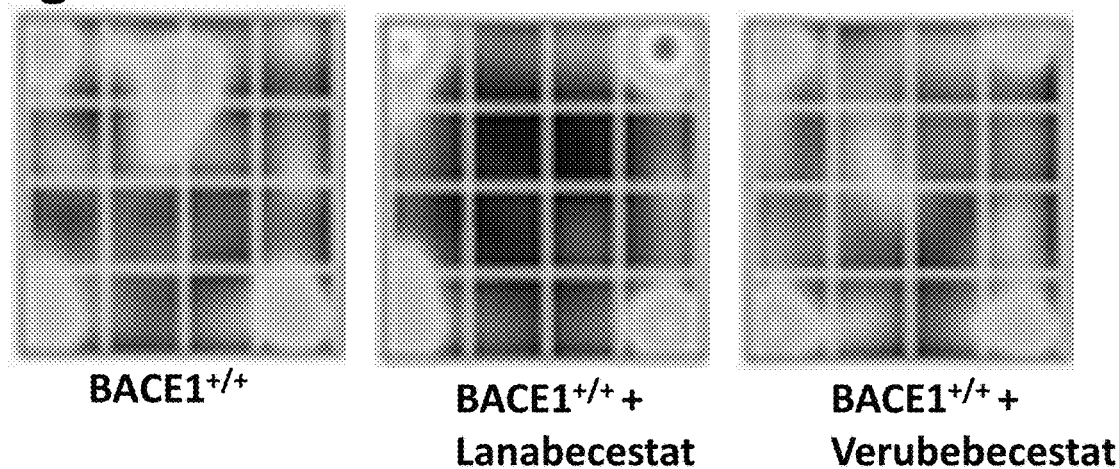
Figure 6D:
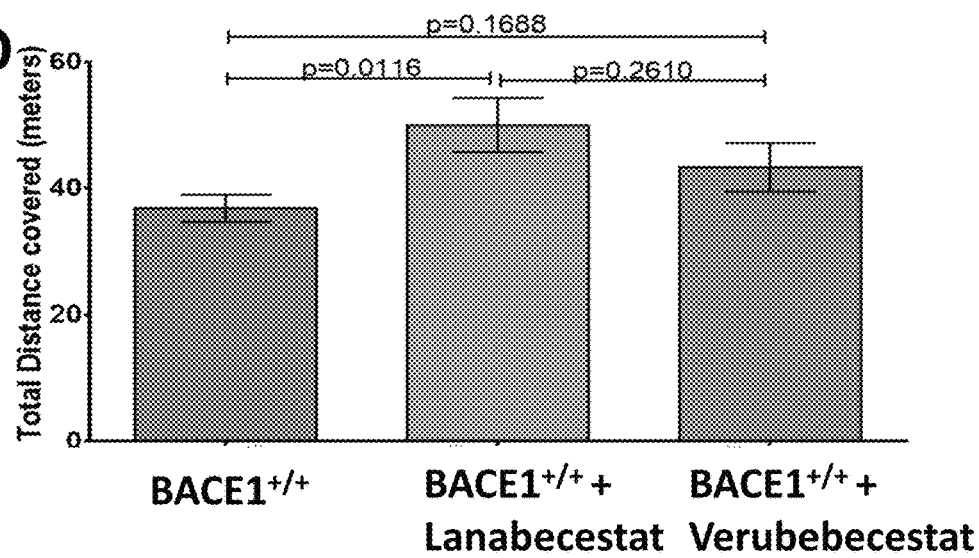
Figure 6E:
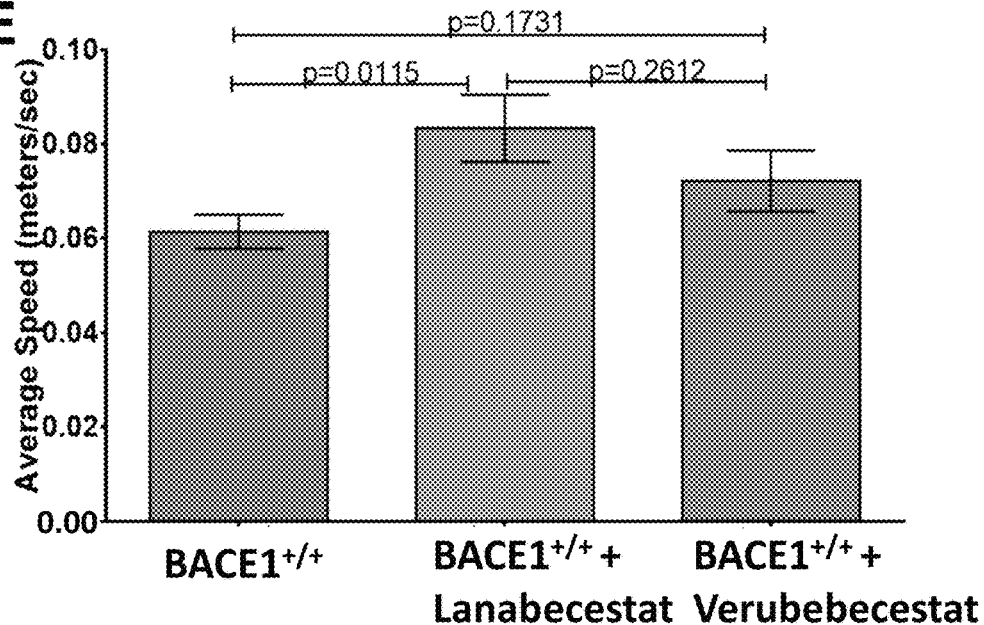
Figure 6F:
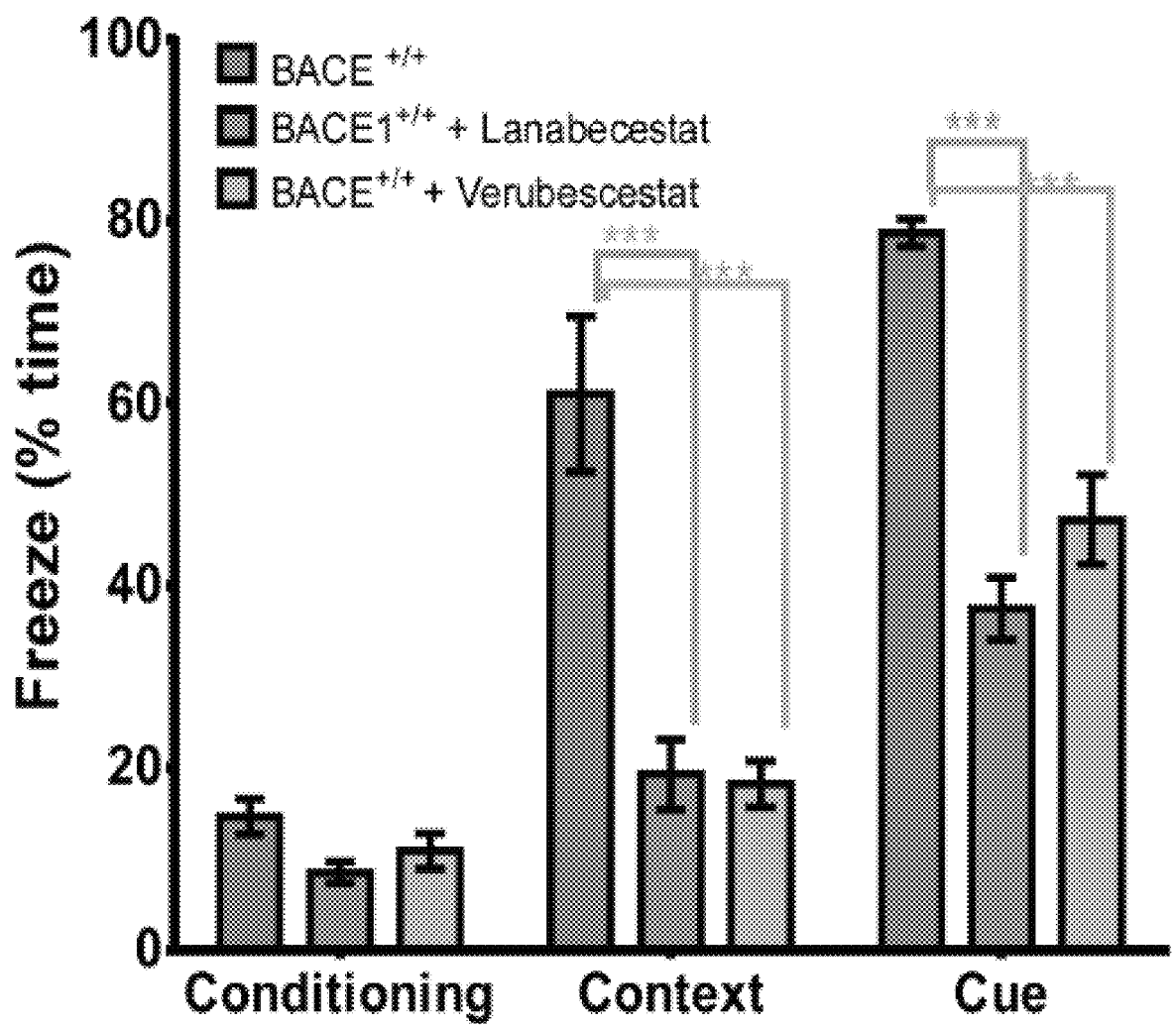
Figure 7:
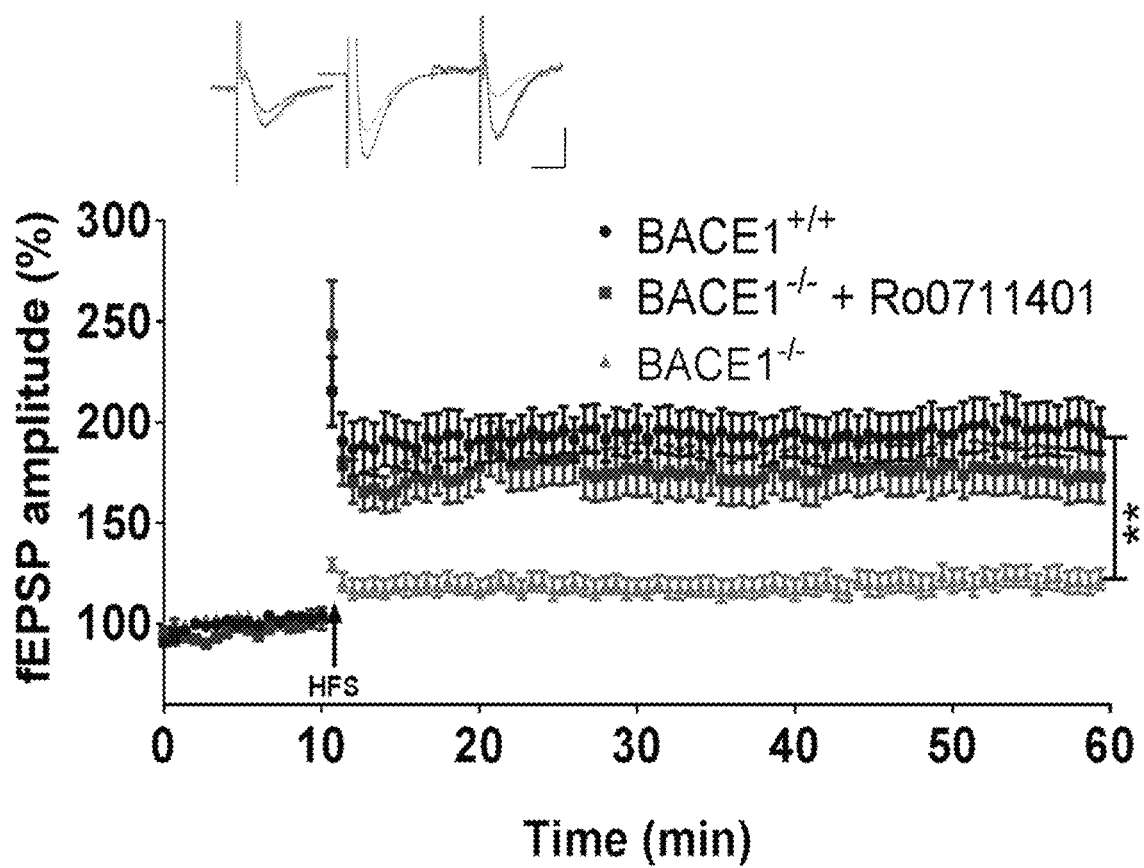
FIG. 7: BACE1 deficiency-mediated LTP reduction is reverted by mGluR1 positive allosteric modulator in mice. LTP was recorded on horizontal hippocampal slices from 16-month-old mice as described above after treatment with Ro0711401 for ~50 days. The LTP in the Ro0711401 treatment group was comparable to WT in this age group and both were significantly higher than BACE1-null mice at 16 months. N=7 slices (4 animals) for BACe1 KO, and N=10 slices (3 animals) for BACE1+Ro0711401, N=8 slices (3 animals) for BACE1 WT (**, P<0.01, student t-test).
Figure 8A:
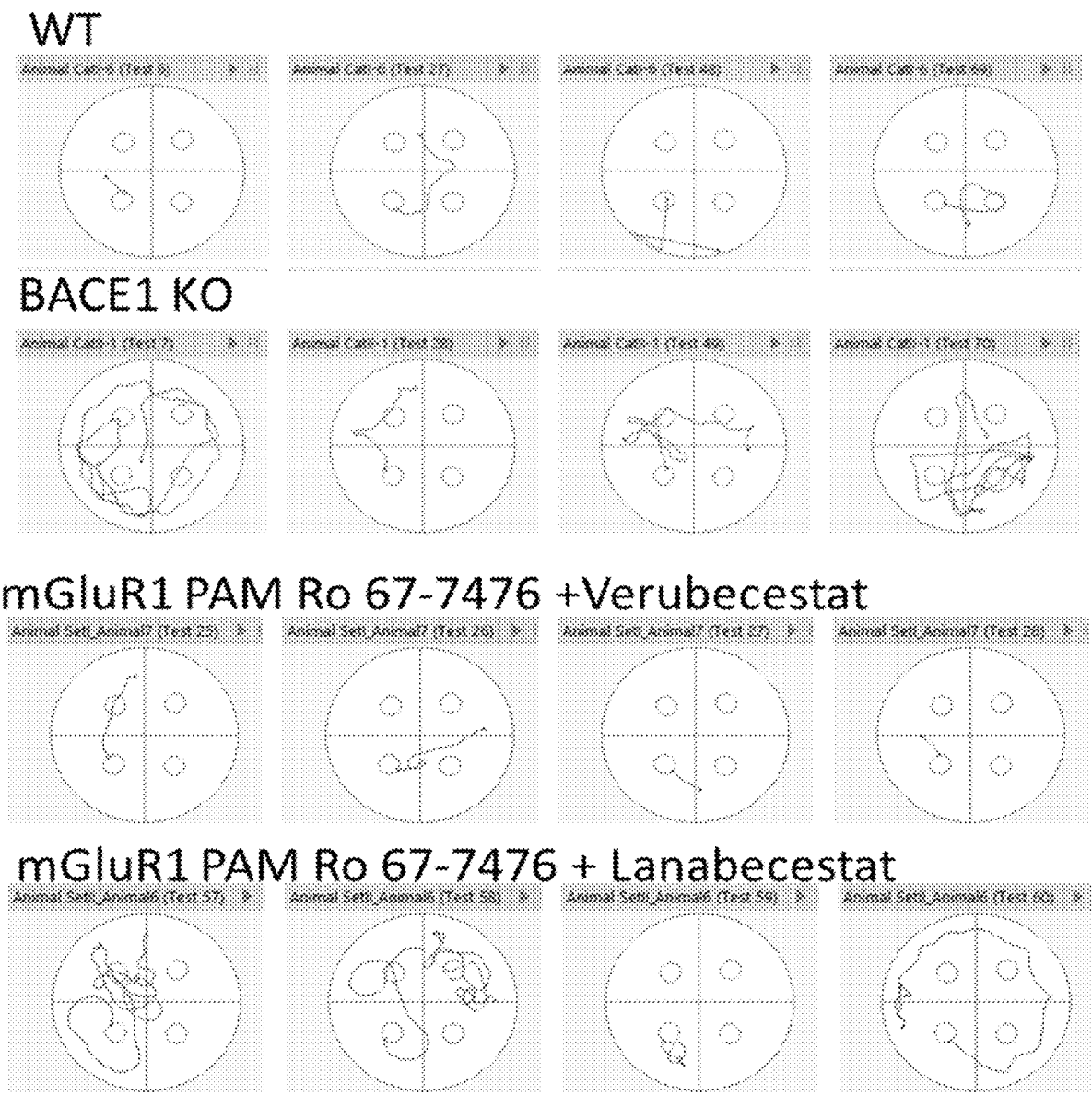
FIG. 8A-8C: Combined therapy with BACE1 inhibitors and mgluR1 PAMs improve spatial memory as observed with Morris water maze. (A) We see improved spatial memory as shown here with track plots with reduced distance in finding hidden platforms with our combined therapy. (B,C) Average duration to reach hidden platforms reduced in both training and testing phase of first 8 days of Morris maze trials in combined drugs specially with Verubecestat at 3 mg/kg vs BACE1 deficient conditions (KO). However Lanabecestat at 0.5 mg/kg with mGluR1 PAM did not show any such improvement. (D) On 9th probe trial treatment with either Verubecestat at 3 mg/kg+mGluR1 PAM or Lanabecestat at 0.5 mg/kg+mGluR1 PAM show improvement over BACE1 KO condition.
Figure 8B:
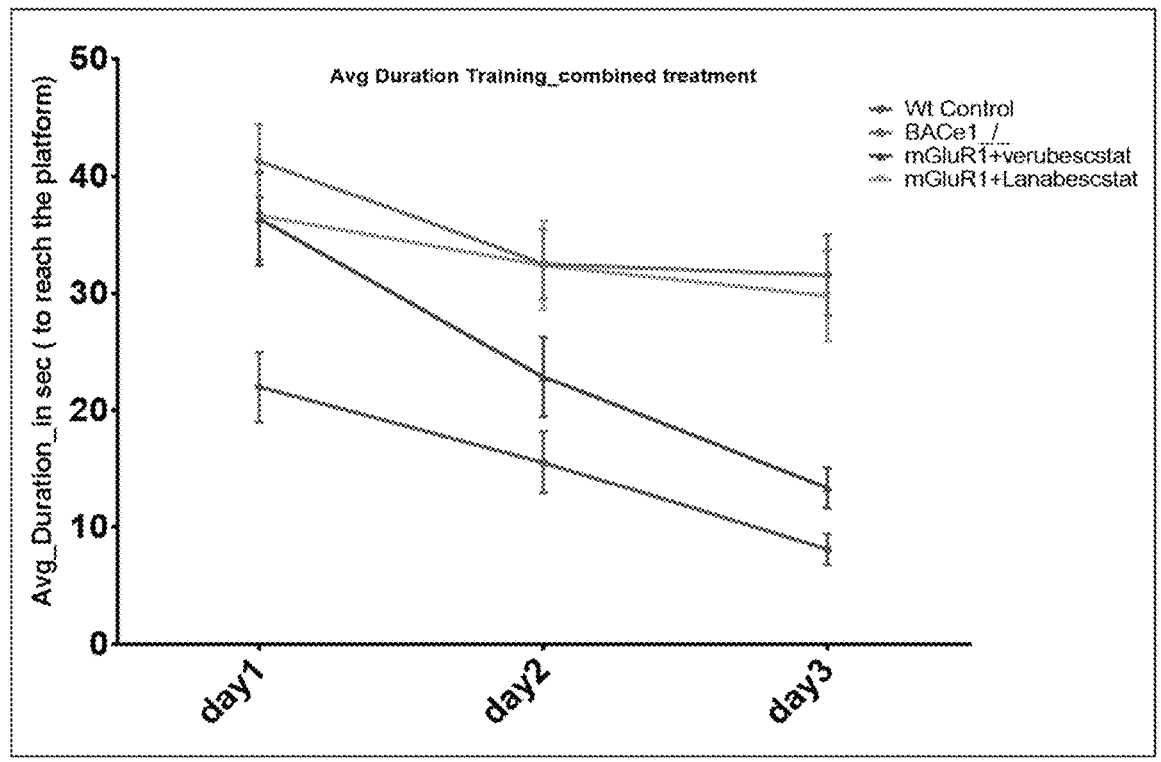
Figure 8C:
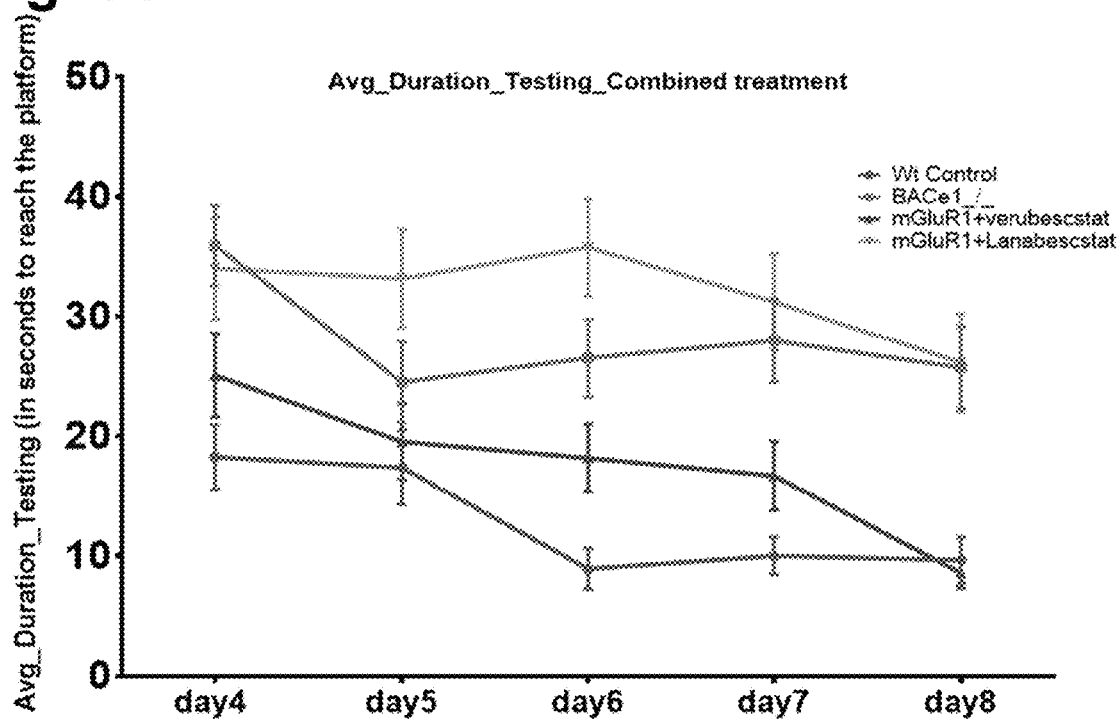
Figure 8D:
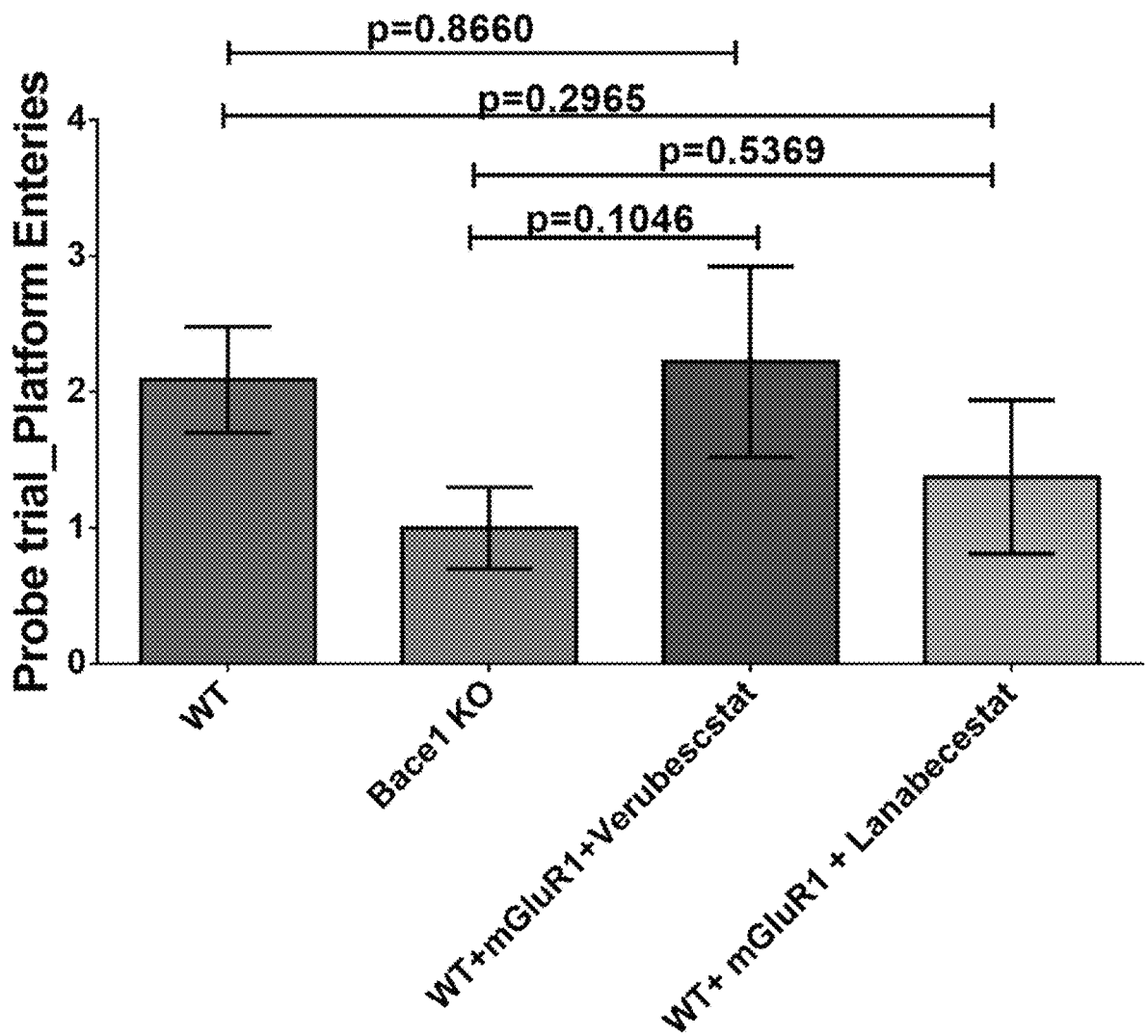

After the behavioral tests, mice were evaluated for their synaptic plasticity measured by LTP, induced by high frequency stimulation (HFS) in hippocampal slices. Consistent with the ameliorated learning and exploratory behaviors, LTP was significantly elevated to the level close to that of WT mice at the age of 14- to15-month old (FIG. 5). Synaptic impairment due to BACE1 deficiency can be significantly reversed when Ro0711401, a potent mGluR1 positive allosteric modulator, is given to mice for about two months.
Impaired Synaptic Plasticity by BACE1 Inhibitors is Mitigated by mGluR Positive Allosteric Modulators To determine if administering BACE1 inhibitors and mGluR PAMs in the same animal would alleviate some of the detrimental effect on LTP, we administered 12 months old BACE1+/+ animals either Verubecestat at 3 mg/kg or Lanabecestat at 0.5 mg/kg by oral gavage daily along with mGluR1 PAM Ro 67-7476 (Tocris Bioscience cat #4346) at 4 mg/kg, i.p. (PMID 27273769), which has similar potency to Ro0711401. After mice were treated either the BACE1 inhibitor alone or PAM Ro 67-7476 alone or the combo for ~50 days, we conducted neural behavioral tests discussed above to assess the impact of cognitive behaviors associated with BACE1 inhibitors. Mice treated with BACE1 inhibitor Verubecestat at 3 mg/kg or Lanabecestat at 0.5 mg/kg not only reduced LTP but also altered impaired learning behaviors. On Y-maze test, we found that mice treated with either Verubecestat or Lanabecestat showed reduction in % of spontaneous alteration, but was not statistical significance (FIG. 5A, p=0.0622 or 0.0695 when compared to mock treatment, N=9, Student t-test). When treated together with Ro 67-7476, the Verubecestat+Ro 67-7476 group showed improvement in spontaneous alternation when compared with mice treated with Verubecestat alone (FIG. 5A, P=0.0334, N=09, Student t-test). Similarly, there was an improvement in the Lanabecestat+Ro 67-7476 group over Lanabecestat alone (FIG. 5A, P=0.036, N=09, Student t-test). Unlike BACE-null mice (FIG. 4A), mice treated with Verubecestat had reduction in total entry, and a further reduction was noted when Ro 67-7476 was included in the treatment (FIG. 5B, P=0.0503 and P=0.2142, N=9, student t-test). This reduction was more significant in mice treated with Lanabecestat either alone or together Ro 67-7476 (FIG. 5B, P=0.0013 and P=0.0001, N=9, student t-test). This result on Y-maze test showed differential effect with BACE1 inhibition compared to BACE1-null mice, indicating potential off-target effects. BACE1-null mice exhibited anxiety behaviors by traveling more on the open field (FIG. 4C), and mice treated with either Verubecestat or Lanabecestat also traveled more distances (FIG. 5C) and faster (FIG. 5D). WT mice treated with combined drug cocktail of BACE1 inhibitors and mGluR1 PAM significantly reduced their traveled distances (FIG. 5C,) moved slower (FIG. 5D, N=9, Student's t-test). We noted that the speed was reduced more in the combined treatment category of Lanabecestat+Ro 67-7476 than in Verubecestat+Ro 67-7476. Mice treated with either Lanabecestat or Verubecestat stayed more in the corner of the open field area than mock-treated controls (FIG. 5E). Adding mGluR1 PAM in the treatment improved in the Verubecestat group and to a lesser extent in the Lanabecestat group.

We further assessed these animals in water maze to test the effect of these cocktail of drugs of BACE1 inhibitors and mGluR1 PAM on hippocampal-dependent learning and memory. Our results showed that Verubecestat+Ro 67-7476 group showed improved performance than Lanabecestat+Ro 67-7476 during both training and testing phase FIG. 8A-D. During probe trial both Verubecestat+Ro 67-7476 (P=0.5369,N=09) and Lanabecestat+Ro 67-7476 (P=0.1046, N=09) group made more attempts to find the platform vs BACE1 KO animals. They were also in the same range of attempts made by the WT animals Verubecestat+Ro 67-7476 (P=0.29659,N=09) and Lanabecestat+Ro 67-7476 (P=0.2965N=09). These data suggests that there is a good improvement in the working memory of the animals treated with the combined drugs.
Discussion BACE1 is a prime target for AD therapy, as it is elevated in the brains of patients with AD and its cleavage of APP is the rate-limiting step in Aβ production. However, clinical trials of BACE1 inhibitors in treating AD patients have not been successful because of failed to improve cognitive functions, despite reducing Aβ plaque formation. Therefore, it is critical to find solutions that will take the advantage of this plaque reduction and can overcome the unwanted side effects associated with worsening cognitive functions/scores. We demonstrate that a group I mGluR positive allosteric modulator in combination with BACE1 inhibitors is promising for treating AD patients.

Here we showed that, by supplementing BACE1-null or mice with BACE1 inhibitors with the mGluR1 positive allosteric modulator Ro0711401 or CHPG, reduced LTP was markedly reversed or mitigated.
Material and Methods:
Animals BACE1-null mice were generated as previously described (Cai et al., 2001) and maintained in a C57BL/6 background. All animal use and procedures were performed according to the Institutional Animal Care and Use (IACUC) protocols at Cleveland Clinic and UConn health Center, Farmington and in compliance with the guidelines established by the Public Health Service Guide for the Care and Use of Laboratory Animals. Animals of either sex were used.
Drug Delivery C57BL/6 mice of either sex (4-6 months of age; n=6 per group) received vehicle or BACE1 inhibitors, Lanabecestat (AZD3293) solution at 0.25 mg/kg or 0.5 mg/kg) via oral gavage (Eketjall et al., 2016b). For Verubescstat, 3mg/kg dose was used and delivered orally via gavage (Kennedy et al., 2016). Treatment usually last 2-4 months. The mGluR1 positive allosteric modulator Ro0711401 at 10 mg/kg was given as intraperitoneal injections (IP) 1 hour before decapitation for LTP experiments (Notartomaso et al., 2013). For behavioral assays, Ro0711401 was deliver via IP injection at 12-hour intervals for 6-8 weeks. The mGluR1/5 positive allosteric modulator CHPG was mixed in aCSF and used during recording LTP. The drug was applied in a bath during baseline recording for at least for 30 minutes before HFS stimulation was applied and LTP was recorded (Le Duigou and Kullmann, 2011).
Western Blotting and Antibodies Synaptosome isolation was performed using Thermo Scientific Syn-PER Synaptic Protein Extraction Reagent (cat #87793) from whole brain samples. Briefly, mice were sacrificed by live decapitation, and rapidly dissected hippocampi were homogenized in Syn-Per reagent, ~1 ml/100 mg tissue. Samples were then centrifuged at 1200×g for 10 min. The resulting supernatant was then centrifuged at 15,000×g for 20 min. Pellets (synaptosomes) were resuspended in buffer B (3 mM sucrose in 6 mm Tris, pH 8.0) with 1% SDS, briefly sonicated, and frozen in −80° C. Total protein extraction was performed according to previously-described procedures (Hu et al., 2007). Brain samples were homogenized in radioimmunoprecipitation assay (RIPA) buffer (50 mM Tris-HCl, pH 7.4, 1% NP-40, 0.25% sodium deoxycholate, 150 mM NaCl, 1 mM EDTA, 1 mM NaF, 1 mM Na3VO4, and a protease inhibitor cocktail [Roche]) and centrifuged at 13,200 rpm for 90 min. Equal amounts of protein were resolved on a NuPAGE Bis-Tris gel (Invitrogen) and transferred onto nitrocellulose membranes (Invitrogen). Subsequently, blots were incubated with primary antibodies 1:1,000 mGluR1 [AB_12551; Cell Signaling]; 1:1,000 PSD-95 [AB_36233; Cell Signaling]; 1:5,000 GluR1 [AB_05-855; Upstate]; 1:1,000 GluR2/3 [AB_07-598; Upstate]; 1:1,000 GluR4 [AB_06-308; Upstate]; 1:1,000 Homer [AB_8231; Cell Signaling]; 1:500 TMEM25 [AB_24361-1-AP; ProteinTech Group]; 1:1,000 Bassoon [AB_141021; Synaptic Systems]; 1:10,000 Actin [AB_A5441; Sigma], overnight at 4° C. After extensive washing, blots were reacted with HRP-conjugated secondary antibodies and visualized using enhanced chemiluminescence (Thermo Scientific).

Slice Preparation

Acute brain slices were prepared as previously described (Hu et al., 2018). Briefly, the mice were decapitated and the brains were immersed in low-calcium artificial cerebrospinal fluid (aCSF) containing (in mM): 125 NaCl, 2.5 KCl, 10 glucose, 25 NaHCO3, 1.25 NaH2PO4, 0.4 L-ascorbic acid, 3 myo-inositol, 2 Na-pyruvate, 3 MgCl2 and 0.1 CaCl2 continuously bubbled with 95% O2 and 5% CO2 (pH≈7.3). Animals were decapitated with a guillotine and the brain was quickly removed to an ice-cold aCSF chamber with constant bubbling of 95% O2 and 5% CO2. Acute horizontal brain slices containing the hippocampus were obtained using a Campden 7000 smz-2 vibratome from 4-7-month-old mice at 350 µm thick. Slices were immediately transferred to an incubation beaker containing normal aCSF (same as the low-calcium aCSF except that 1 mM MgCl2 and 1, 1.2, or 2 mM CaCl2 were used) at 30° C., continuously bubbled with 95% O2 and 5% CO2. Slices were allowed to recover for 1 hour and then were transferred to an MED-64 recording chamber with the same aCSF solution at ≈30° C., maintained by MED ThermoConnector (Automate Scientific) with continuous aCSF perfusion at 2 ml/min.

LTP Recordings

LTP recordings on hippocampal slices were performed according to previously-described procedures (Shimono et al., 2002; Baba et al., 2003; Itoh et al., 2005). Upon obtaining horizontal hippocampal slices from the brains of mice, the prepared slices were then placed onto the center of an MED probe (MED-P515A; AutoMate™ Scientific) with continuous perfusion of aCSF and bubbling of 95% O2 and 5% CO2. The device has an array arranged in an 8×8 pattern of 64 planar microelectrodes across a hippocampal slice. Each electrode is 20×20 µm with an interelectrode distance of 150 µm. A MED-A64HE1S head amplifier and a MED-A64MD1 main amplifier, run by Mobius software, were used for data acquisition and analysis. SCs to CA1 synapses were typically analyzed for LTP assays. fEPSPs caused by stimulation were recorded at a 20-kHz sampling rate within the CA1 subregion of the hippocampus. Control fEPSPs were recorded for at least 10 min before the conditioning stimulation, using a response ~50% of the maximum. After a stable baseline was established, LTP was induced with three trains of 100 Hz for 1 s with an intertrain interval F of 20 s. Field potential amplitudes were then measured. Data are expressed as mean±SEM. Synaptic strength was evaluated by measuring changes in the fEPSP amplitude relative to baseline. Statistics were calculated by Student's t tests.

Y Maze

Spontaneous alternations were tested as described previously (Holcomb et al., 1998). This learning task does not involve any training, reward, or punishment and allows the assessment of spatial working memory that is dependent upon the hippocampus. The symmetrical Y maze made of acrylic consists of three arms separated by 120 degrees. Each arm is 40 cm long, 17 cm high, 4 cm wide at the bottom and 13 cm wide at the top. Each mouse was placed in the center of the Y maze and was allowed to explore freely through the maze during a 5 min session. The sequence and total number of arms entered was recorded. Arm entry was considered to be completed when the hind paws of the mouse had been completely placed in the arm. Percentage of alternations is the number of triads containing entries into all three arms divided by the maximum possible alternations (the total number of arms entered minus 2)×100. Statistics were calculated by Student's t tests.

Open Field

The square white open-field arena had a diameter of 100 cm and 55-cm-high sidewalls. Each subject was released in the middle of the arena and observed for 10 minutes. Performance in the open field was recorded by a computer-based video tracking system (Any maze™ software, San Diego instruments, USA). Activity measures included distance traveled, percentage of time spent in corners vs. the center of the arena, and speed of movement during active exploration. The number of entries to the central zone of the open field was also recorded. Statistics were calculated by Student's t tests.

Morris Water Maze

The Morris water maze test was used to assess cognitive impairment. The apparatus consisted of a white circular tank (120 cm in diameter and 40 cm deep) filled with warm water (22° C.). The water was made to appear opaque using white nontoxic paint. A transparent platform (8 cm in diameter) was located in the middle of the southwest quadrant. Mice were subjected to four consecutive trials each day over a 3-day training period (with a flag attached to the platform) and then again for 5 days (no flag attached to platform) and the platform was submerged 0.5 cm below the water surface. Each mouse was released from four different positions around the perimeter of the tank (north, northwest, east, and southeast). In each trial, every mouse was allowed to swim until it found the platform (for a maximum of 60 s) and was subsequently left on the platform for 20 s between trials. If the platform was not found in 60 s, the mouse was guided to the platform and remained there for 20 s. The escape latency to find the hidden platform was automatically recorded using a video tracking system (Any-maze, San Diego instruments). At the end of the training on the eighth day, a probe test was conducted for 30 s on the 9th day. The platform was removed; each was released from the northeast quadrant and was allowed to swim for 60 s. Memory retention was measured by quantifying the time spent in the target quadrant, the number of entries made into the southwest quadrant, and the number of crossings over the previous platform location. Statistics were calculated by Student's t tests. Values are expressed as mean±SEM.

REFERENCES

Baba A, Yasui T, Fujisawa S, Yamada R X, Yamada M K, Nishiyama N, Matsuki N, Ikegaya Y (2003) Activity-evoked capacitative Ca2+ entry: implications in synaptic plasticity. The Journal of neuroscience : the official journal of the Society for Neuroscience 23:7737-7741.

Brown J T, Richardson J C, Collingridge G L, Randall A D, Davies C H (2005) Synaptic transmission and synchronous activity is disrupted in hippocampal slices taken from aged TAS10 mice. Hippocampus 15:110-117.

Byrnes K R, Loane D J, Faden A I (2009) Metabotropic glutamate receptors as targets for multipotential treatment of neurological disorders. Neurotherapeutics: the journal of the American Society for Experimental NeuroTherapeutics 6:94-107.

Cai H, Wang Y, McCarthy D, Wen H, Borchelt D R, Price D L, Wong P C (2001) BACE1 is the major beta-secretase for generation of Abeta peptides by neurons. Nature neuroscience 4:233-234.

Chapman P F, White G L, Jones M W, Cooper-Blacketer D, Marshall V J, Irizarry M, Younkin L, Good M A, Bliss T V, Hyman B T, Younkin S G, Hsiao K K (1999) Impaired synaptic plasticity and learning in aged amyloid precursor protein transgenic mice. Nature neuroscience 2:271-276.

Corriveau R A et al. (2017) Alzheimer's Disease-Related Dementias Summit 2016: National research priorities. Neurology 89:2381-2391.

D'Amore V, Santolini I, Celli R, Lionetto L, De Fusco A, Simmaco M, van Rijn C M, Vieira E, Stauffer S R, Conn P J, Bosco P, Nicoletti F, van Luijtelaar G, Ngomba R T (2014) Head-to head comparison of mGlu1 and mGlu5 receptor activation in chronic treatment of absence epilepsy in WAG/Rij rats. Neuropharmacology 85:91-103.

Das B, Yan R (2019) A Close Look at BACE1 Inhibitors for Alzheimer's Disease Treatment. CNS Drugs 33:251-263.

Dickstein D L, Weaver C M, Luebke J I, Hof P R (2013) Dendritic spine changes associated with normal aging. Neuroscience 251:21-32.

Dobrowolska Zakaria J A, Vassar R J (2018) A promising, novel, and unique BACE1 inhibitor emerges in the quest to prevent Alzheimer's disease. EMBO Mol Med 10.

Dubois B et al. (2016) Preclinical Alzheimer's disease: Definition, natural history, and diagnostic criteria. Alzheimer's & dementia: the journal of the Alzheimer's Association 12:292-323.

Egan M F, Kost J, Tariot P N, Aisen P S, Cummings J L, Vellas B, Sur C, Mukai Y, Voss T, Furtek C, Mahoney E, Harper Mozley L, Vandenberghe R, Mo Y, Michelson D (2018) Randomized Trial of Verubecestat for Mild-to-Moderate Alzheimer's Disease. N Engl J Med 378:1691-1703.

Egan M F, Kost J, Voss T, Mukai Y, Aisen P S, Cummings J L, Tariot P N, Vellas B, van Dyck C H, Boada M, Zhang Y, Li W, Furtek C, Mahoney E, Harper Mozley L, Mo Y, Sur C, Michelson D (2019) Randomized Trial of Verubecestat for Prodromal Alzheimer's Disease. N Engl J Med 380:1408-1420.

Eketjall S, Janson J, Kaspersson K, Bogstedt A, Jeppsson F, Falting J, Haeberlein S B, Kugler A R, Alexander R C, Cebers G (2016a) AZD3293: A Novel, Orally Active BACE1 Inhibitor with High Potency and Permeability and Markedly Slow Off-Rate Kinetics. J Alzheimers Dis 50:1109-1123.

Eketjall S, Janson J, Kaspersson K, Bogstedt A, Jeppsson F, Falting J, Haeberlein S B, Kugler A R, Alexander R C, Cebers G (2016b) AZD3293: A Novel, Orally Active BACE1 Inhibitor with High Potency and Permeability and Markedly Slow Off-Rate Kinetics. Journal of Alzheimer's disease: JAD 50:1109-1123.

Evin G, Hince C (2013) BACE1 as a therapeutic target in Alzheimer's disease: rationale and current status. Drugs & aging 30:755-764.

Filser S, Ovsepian S V, Masana M, Blazquez-Llorca L, Brandt E A, Volbracht C, Muller M B, Jung C K, Herms J (2015) Pharmacological inhibition of BACE1 impairs synaptic plasticity and cognitive functions. Biol Psychiatry 77:729-739.

Fitzjohn S M, Morton R A, Kuenzi F, Rosahl T W, Shearman M, Lewis H, Smith D, Reynolds D S, Davies C H, Collingridge G L, Seabrook G R (2001) Age-related impairment of synaptic transmission but normal long-term potentiation in transgenic mice that overexpress the human APP695SWE mutant form of amyloid precursor protein. The Journal of neuroscience: the official journal of the Society for Neuroscience 21:4691-4698.

Gong Q Z, Phillips L L, Lyeth B G (1999) Metabotropic glutamate receptor protein alterations after traumatic brain injury in rats. Journal of neurotrauma 16:893-902.

Holcomb L, Gordon M N, McGowan E, Yu X, Benkovic S, Jantzen P, Wright K, Saad I, Mueller R, Morgan D, Sanders S, Zehr C, O'Campo K, Hardy J, Prada C M, Eckman C, Younkin S, Hsiao K, Duff K (1998) Accelerated Alzheimer-type phenotype in transgenic mice carrying both mutant amyloid precursor protein and presenilin 1 transgenes. Nature medicine 4:97-100.

Hu X, Das B, Hou H, He W, Yan R (2018) BACE1 deletion in the adult mouse reverses preformed amyloid deposition and improves cognitive functions. The Journal of experimental medicine 215:927-940.

Hu X, Shi Q, Zhou X, He W, Yi H, Yin X, Gearing M, Levey A, Yan R (2007) Transgenic mice overexpressing reticulon 3 develop neuritic abnormalities. EMBO J 26:2755-2767.

Hussain I, Powell D, Howlett D R, Tew D G, Meek T D, Chapman C, Gloger I S, Murphy K E, Southan C D, Ryan D M, Smith T S, Simmons D L, Walsh F S, Dingwall C, Christie G (1999) Identification of a novel aspartic protease (Asp 2) as beta-secretase. Molecular and cellular neurosciences 14:419-427.

Itoh K, Shimono K, Lemmon V (2005) Dephosphorylation and internalization of cell adhesion molecule L1 induced by theta burst stimulation in rat hippocampus. Mol Cell Neurosci 29:245-249.

Jack C R, Jr., Knopman D S, Jagust W J, Petersen R C, Weiner M W, Aisen P S, Shaw L M, Vemuri P, Wiste H J, Weigand S D, Lesnick T G, Pankratz V S, Donohue M C, Trojanowski J Q (2013) Tracking pathophysiological processes in Alzheimer's disease: an updated hypothetical model of dynamic biomarkers. Lancet Neurol 12:207-216.

Kammermeier P J (2012) The orthosteric agonist 2-chloro-5-hydroxyphenylglycine activates mGluR5 and mGluR1 with similar efficacy and potency. BMC Pharmacol 12:6.

Kennedy M E et al. (2016) The BACE1 inhibitor verubecestat (MK-8931) reduces CNS beta-amyloid in animal models and in Alzheimer's disease patients. Sci Transl Med 8:363ra150.

Kumar A (2011) Long-Term Potentiation at CA3-CA1 Hippocampal Synapses with Special Emphasis on Aging, Disease, and Stress. Frontiers in aging neuroscience 3:7.

Le Duigou C, Kullmann D M (2011) Group I mGluR agonist-evoked long-term potentiation in hippocampal oriens interneurons. The Journal of neuroscience: the official journal of the Society for Neuroscience 31:5777-5781.

Lin X, Koelsch G, Wu S, Downs D, Dashti A, Tang J (2000) Human aspartic protease memapsin 2 cleaves the beta-secretase site of beta-amyloid precursor protein. Proceedings of the National Academy of Sciences of the United States of America 97:1456-1460.

Loane D J, Stoica B A, Byrnes K R, Jeong W, Faden A I (2013) Activation of mGluR5 and inhibition of NADPH oxidase improves functional recovery after traumatic brain injury. Journal of neurotrauma 30:403-412.

Luscher C, Huber K M (2010) Group 1 mGluR-dependent synaptic long-term depression: mechanisms and implications for circuitry and disease. Neuron 65:445-459.

Ngomba R T, Santolini I, Salt T E, Ferraguti F, Battaglia G, Nicoletti F, van Luijtelaar G (2011) Metabotropic glutamate receptors in the thalamocortical network: strategic targets for the treatment of absence epilepsy. Epilepsia 52:1211-1222.

Notartomaso S, Zappulla C, Biagioni F, Cannella M, Bucci D, Mascio G, Scarselli P, Fazio F, Weisz F, Lionetto L, Simmaco M, Gradini R, Battaglia G, Signore M, Puliti A, Nicoletti F (2013) Pharmacological enhancement of mGlu1 metabotropic glutamate receptors causes a prolonged symptomatic benefit in a mouse model of spinocerebellar ataxia type 1. Molecular brain 6:48.

Ou-Yang M-H, Kurz J E, Nomura T, Popovic J, Rajapaksha T W, Dong H, Contractor A, Chetkovich D M, Tourtellotte W G, Vassar R (2018) Axonal organization defects in the hippocampus of adult conditional BACE1 knockout mice. Science translational medicine 10.

Reiner A, Levitz J (2018) Glutamatergic Signaling in the Central Nervous System: Ionotropic and Metabotropic Receptors in Concert. Neuron 98:1080-1098.

Selkoe D J, Hardy J (2016) The amyloid hypothesis of Alzheimer's disease at 25 years. EMBO Mol Med 8:595-608.

Shimono K, Kubota D, Brucher F, Taketani M, Lynch G (2002) Asymmetrical distribution of the Schaffer projections within the apical dendrites of hippocampal field CA1. Brain Res 950:279-287.

Sinha S et al. (1999) Purification and cloning of amyloid precursor protein beta-secretase from human brain. Nature 402:537-540.

Vassar R (2019) Editorial: Implications for BACE1 Inhibitor Clinical Trials: Adult Conditional BACE1 Knockout Mice Exhibit Axonal Organization Defects in the Hippocampus. J Prev Alzheimers Dis 6:78-84.

Vassar R et al. (1999) Beta-secretase cleavage of Alzheimer's amyloid precursor protein by the transmembrane aspartic protease BACE. Science 286:735-741.

Wang H, Song L, Laird F, Wong P C, Lee H K (2008) BACE1 knock-outs display deficits in activity-dependent potentiation of synaptic transmission at mossy fiber to CA3 synapses in the hippocampus. J Neurosci 28:8677-8681.

Wang H, Song L, Lee A, Laird F, Wong P C, Lee H K (2010) Mossy fiber long-term potentiation deficits in BACE1 knock-outs can be rescued by activation of alpha7 nicotinic acetylcholine receptors. J Neurosci 30:13808-13813.

Witton J, Brown J T, Jones M W, Randall A D (2010) Altered synaptic plasticity in the mossy fibre pathway of transgenic mice expressing mutant amyloid precursor protein. Molecular brain 3:32.

Yan R, Vassar R (2014) Targeting the beta secretase BACE1 for Alzheimer's disease therapy. Lancet Neurol 13:319-329.

Yan R, Bienkowski M J, Shuck M E, Miao H, Tory M C, Pauley A M, Brashier J R, Stratman N C, Mathews W R, Buhl A E, Carter D B, Tomasselli A G, Parodi L A, Heinrikson R L, Gurney M E (1999) Membrane-anchored aspartyl protease with Alzheimer's disease beta-secretase activity. Nature 402:533-537.

We claim:

1. A method for improving cognitive function in a subject with a disorder selected from Alzheimer's disease (AD), Down's syndrome, Parkinson's disease, vascular dementia, Dementia with Lewy Bodies, and/or frontal temporal dementia, comprising administering to the subject, an amount effective to treat the disorder of:
(a) a Beta site APP Cleaving Enzyme 1 (BACE1) inhibitor selected from the group consisting of SCH1682496, 6-(3-chloro-5-(5-prop-1-yn-1-yl)pyridin-3-yl)thiophen-2-yl)-2-imino-3,6-dimethyltetrahydropyrimidin-4(1H)-one, LY2811376, verubecestat, lanabecestat, umibecestat, elenbecestat, atabecestat, LY3202626, and AZD3839, or a pharmaceutically acceptable salt thereof; and
(b) a metabotropic glutamate receptor (mGluR) agonist selected from the group consisting of (R,S)-2-chloro-5-hydroxyphenylglycine (CHPG), 3-chloro-4-[(5-chloro-2-pyridinyl)oxy]phenyl]-2-pyridinecarboxamide (VU 0422288), (S)-3,5-dihydroxyphenylglycine (DHPG), (R,S)-3,5-dihydroxyphenylglycine, quisqualate, trans-azetidine-2,3-dicarboxylic acid, 3-hydroxyphenylglycine, VU6000799, VU6000790, ACPT1, (R,S)-PPG, Ro 67-7476, and Ro0711401, or a pharmaceutically acceptable salt thereof.

2. The method of claim 1, wherein the BACE1 inhibitor is verubecestat, or a pharmaceutically acceptable salt thereof.

3. The method of claim 1, wherein the mGluR agonist is selected from the group consisting of (R,S)-2-chloro-5-hydroxyphenylglycine (CHPG), (S)-3,5-dihydroxyphenylglycine (DHPG), (R,S)-3,5-dihydroxyphenylglycine, quisqualate, trans-azetidine-2,3-dicarboxylic acid, 3-hydroxyphenylglycine, VU6000799, VU6000790, Ro 67-7476, and Ro0711401.

4. The method of claim 1, wherein the mGluR agonist is Ro0711401, or a pharmaceutically acceptable salt thereof.

5. The method of claim 1, wherein the BACE1 inhibitor and the mGluR agonist are co-administered.

6. The method of claim 1, wherein the BACE1 inhibitor and the mGluR agonist are administered sequentially.

7. The method of claim 1, wherein the subject has Alzheimer's disease (AD).

8. The method of claim 1, wherein the subject has Down's syndrome.

9. The method of claim 1, wherein the subject has Parkinson's disease.

10. The method of claim 1, wherein the subject has dementia.

11. The method of claim 1, wherein the subject is a human subject.

12. The method of claim 11, wherein human subject possesses an apolipoprotein E (APOE) ε4 allele.

13. The method of claim 11, wherein the human subject possesses mutations associated with AD disease incidence and/or progression in one or more of an amyloid precursor protein (APP) gene, a presenilin 1 (PS1) gene, and a Trem 2 gene.

14. The method of claim 1, wherein the BACE1 inhibitor is verubecestat and the mGluR agonist is Ro0711401.

15. The method of claim 14, wherein the disorder is Alzheimer's disease.

* * * * *

UNITED STATES PATENT AND TRADEMARK OFFICE
CERTIFICATE OF CORRECTION

| | |
|---|---|
| PATENT NO. | : 12,156,879 B2 |
| APPLICATION NO. | : 17/108227 |
| DATED | : December 3, 2024 |
| INVENTOR(S) | : Riqiang Yan and Brati Das |

Page 1 of 1

It is certified that error appears in the above-identified patent and that said Letters Patent is hereby corrected as shown below:

In the Specification

At Column 1, replace Lines 11 to 16 with:
--STATEMENT REGARDING FEDERALLY SPONSORED RESEARCH
This invention was made with government support under AG046929, and NS074256 awarded by the National Institutes of Health. The government has certain rights in the invention.--

Signed and Sealed this
Thirteenth Day of January, 2026

John A. Squires
*Director of the United States Patent and Trademark Office*